(12) United States Patent
Commons et al.

(10) Patent No.: US 7,186,749 B2
(45) Date of Patent: Mar. 6, 2007

(54) PYRROLO-NAPHTHYL ACIDS AND METHODS FOR USING THEM

(75) Inventors: Thomas J. Commons, Wayne, PA (US); Douglas John Jenkins, Collegeville, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/208,775

(22) Filed: Aug. 22, 2005

(65) Prior Publication Data

US 2006/0052349 A1 Mar. 9, 2006

Related U.S. Application Data

(60) Provisional application No. 60/603,766, filed on Aug. 23, 2004.

(51) Int. Cl.
*A01N 43/36* (2006.01)
*C07D 257/02* (2006.01)
*C07D 207/323* (2006.01)

(52) U.S. Cl. ............. 514/427; 514/408; 514/381; 514/422; 548/518; 548/563; 548/560; 548/252; 548/253

(58) Field of Classification Search .......... 514/427; 548/560, 235, 314.7, 202; 546/268.1
See application file for complete search history.

(56) References Cited

U.S. PATENT DOCUMENTS

| | | | |
|---|---|---|---|
| 3,026,325 A | 3/1962 | Heinzelman et al. | 548/496 |
| 3,476,770 A | 11/1969 | Scherrer | 548/494 |
| 3,557,142 A | 1/1971 | Bell | 548/516 |
| 3,843,683 A | 10/1974 | Bell | 548/493 |
| 4,478,819 A | 10/1984 | Hercelin et al. | 424/457 |
| 4,736,043 A | 4/1988 | Michel et al. | 548/492 |
| 4,851,406 A | 7/1989 | Martens et al. | 514/217.04 |
| 5,164,372 A | 11/1992 | Matsuo et al. | 514/19 |
| 5,234,917 A | 8/1993 | Finkelstein et al. | 514/397 |
| 5,420,289 A | 5/1995 | Musser et al. | 548/159 |
| 5,482,960 A | 1/1996 | Berryman | 514/414 |
| 5,502,187 A | 3/1996 | Ayer et al. | 544/117 |
| 5,532,276 A | 7/1996 | Mederski et al. | 514/303 |
| 5,541,343 A | 7/1996 | Himmelsbach et al. | 514/424 |
| 5,562,859 A | 10/1996 | Schlosser et al. | 252/299.61 |
| 5,612,360 A | 3/1997 | Boyd et al. | 514/381 |
| 5,693,637 A | 12/1997 | Klinge et al. | 514/221 |
| 5,723,499 A | 3/1998 | Charpentier et al. | 514/717 |
| 5,859,044 A | 1/1999 | Dow et al. | 514/419 |
| 5,883,090 A | 3/1999 | Dorsch et al. | 514/222.5 |
| 5,952,382 A | 9/1999 | Bernardon | 514/569 |
| 6,048,875 A | 4/2000 | De Nanteuil et al. | 514/314 |
| 6,110,963 A | 8/2000 | Malamas | 514/443 |
| 6,137,002 A | 10/2000 | Fisher et al. | 562/440 |
| 6,166,069 A | 12/2000 | Malamas et al. | 514/469 |
| 6,225,328 B1 | 5/2001 | Bernardon | 514/356 |
| 6,232,322 B1 | 5/2001 | Malamas et al. | 514/303 |
| 6,251,936 B1 | 6/2001 | Wrobel et al. | 514/443 |
| 6,302,837 B1 | 10/2001 | De Nanteuil et al. | 514/337 |
| 6,479,524 B1 | 11/2002 | Priepke et al. | 514/352 |
| 6,586,453 B2 | 7/2003 | Dhanoa et al. | 514/365 |
| 6,599,929 B2 | 7/2003 | Cho et al. | 514/415 |
| 6,787,556 B1 | 9/2004 | Hargreaves et al. | 514/311 |
| 6,800,645 B1 | 10/2004 | Cox et al. | 514/314 |
| 6,800,654 B2 | 10/2004 | Mayer et al. | 514/381 |
| 6,844,358 B2 | 1/2005 | Malamas et al. | 514/336 |
| 2003/0013732 A1 | 1/2003 | Elokdah | 514/301 |
| 2003/0018067 A1 | 1/2003 | Elokdah et al. | 514/469 |
| 2003/0060497 A1 | 3/2003 | Gerlach et al. | 514/414 |
| 2003/0125371 A1 | 7/2003 | Elokdah et al. | 514/419 |
| 2004/0116488 A1 | 6/2004 | Jennings et al. | 514/374 |
| 2004/0116504 A1 | 6/2004 | Elokdah et al. | 514/419 |
| 2004/0122070 A1 | 6/2004 | Jennings | 514/374 |
| 2004/0138283 A1 | 7/2004 | Jennings et al. | 514/414 |
| 2004/0204417 A1 | 10/2004 | Perez et al. | 514/249 |
| 2005/0070584 A1 | 3/2005 | Havran et al. | 514/357 |
| 2005/0070585 A1 | 3/2005 | Elokdah et al. | 514/364 |
| 2005/0070587 A1 | 3/2005 | Elokdah et al. | 514/381 |
| 2005/0070592 A1 | 3/2005 | Gundersen | 514/415 |
| 2005/0096377 A1 | 5/2005 | Hu | 514/419 |
| 2005/0113428 A1 | 5/2005 | Gopalsamy et al. | 514/364 |

(Continued)

FOREIGN PATENT DOCUMENTS

DE 3147276 A1 6/1983

(Continued)

OTHER PUBLICATIONS

Aggarwal et al., "A catalytic antibody programmed for torsional activation of amide bond hydrolysis," *Chem. Eur. J.*, Jan. 25, 2003, 9(13), 3132-3142.

(Continued)

*Primary Examiner*—Joseph K. McKane
*Assistant Examiner*—Yong Chu
(74) *Attorney, Agent, or Firm*—Woodcock Washburn LLP

(57) ABSTRACT

The present invention relates to pyrrolo-naphthyl compounds of the formula

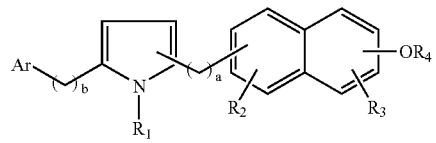

and methods of using them to modulate PAI-1 expression and to treat PAI-1 related disorders.

24 Claims, No Drawings

U.S. PATENT DOCUMENTS

| | | | |
|---|---|---|---|
| 2005/0113436 A1 | 5/2005 | Elokdah et al. | 514/411 |
| 2005/0113438 A1 | 5/2005 | Hu et al. | 514/414 |
| 2005/0113439 A1 | 5/2005 | Hu | 514/414 |
| 2005/0119296 A1 | 6/2005 | Elokdah et al. | 514/300 |
| 2005/0119326 A1 | 6/2005 | Havran et al. | 514/414 |
| 2005/0119327 A1 | 6/2005 | Hu | 514/414 |
| 2005/0215626 A1 | 9/2005 | Havran et al. | 514/469 |
| 2006/0020003 A1 | 1/2006 | Commons et al. | 514/374 |
| 2006/0052348 A1 | 3/2006 | Commons et al. | 514/92 |
| 2006/0052420 A1 | 3/2006 | Commons | 514/340 |

FOREIGN PATENT DOCUMENTS

| | | |
|---|---|---|
| DE | 43 38 770 A1 | 5/1995 |
| DE | 4341453 A1 | 6/1995 |
| DE | 4341665 A1 | 6/1995 |
| DE | 19543639 A1 | 5/1997 |
| DE | 19753522 | 6/1999 |
| EP | 0 416 609 A2 | 3/1991 |
| EP | 0 445 811 A2 | 9/1991 |
| EP | 0 505 111 A2 | 9/1992 |
| EP | 0 508 723 A1 | 10/1992 |
| EP | 0 512 570 A1 | 11/1992 |
| EP | 0 512 675 A1 | 11/1992 |
| EP | 0 540 956 A1 | 5/1993 |
| EP | 0 560 407 A1 | 9/1993 |
| EP | 0 655 439 A2 | 5/1995 |
| EP | 0 720 982 A1 | 7/1996 |
| EP | 0 759 434 A1 | 2/1997 |
| EP | 0 819 686 A1 | 1/1998 |
| EP | 0 822 185 A1 | 2/1998 |
| EP | 0 955 299 A1 | 11/1999 |
| EP | 1 092 716 | 4/2001 |
| EP | 1 156 045 A1 | 11/2001 |
| GB | 1 321 433 | 6/1973 |
| JP | 2002-275157 | 9/2002 |
| JP | 2004-250400 | 9/2004 |
| JP | 2004-250401 | 9/2004 |
| WO | 91/00277 A1 | 1/1991 |
| WO | 93/10114 A1 | 5/1993 |
| WO | 94/00120 A1 | 1/1994 |
| WO | 94/13637 A1 | 6/1994 |
| WO | 94/14434 A1 | 7/1994 |
| WO | 94/26738 A1 | 11/1994 |
| WO | 95/10513 A1 | 4/1995 |
| WO | 96/06840 A1 | 3/1996 |
| WO | 96/19469 A1 | 6/1996 |
| WO | 96/21656 A1 | 7/1996 |
| WO | 96/26207 A1 | 8/1996 |
| WO | 96/32379 A1 | 10/1996 |
| WO | 97/04774 A1 | 2/1997 |
| WO | 97/09308 A1 | 3/1997 |
| WO | 97/28159 A1 | 8/1997 |
| WO | 97/43260 A1 | 11/1997 |
| WO | 97/48697 A1 | 12/1997 |
| WO | 98/08818 A1 | 3/1998 |
| WO | 99/18099 A1 | 4/1999 |
| WO | 99/28297 A1 | 6/1999 |
| WO | 99/43651 A2 | 9/1999 |
| WO | 99/43654 A2 | 9/1999 |
| WO | 99/43672 A1 | 9/1999 |
| WO | 99/46260 A1 | 9/1999 |
| WO | 99/50268 A1 | 10/1999 |
| WO | 99/58511 A1 | 11/1999 |
| WO | 99/58519 A1 | 11/1999 |
| WO | 99/61435 A1 | 12/1999 |
| WO | 00/18764 A1 | 4/2000 |
| WO | 00/32180 A2 | 6/2000 |
| WO | 00/35919 A1 | 6/2000 |
| WO | 00/46195 A1 | 8/2000 |
| WO | 00/46197 A1 | 8/2000 |
| WO | 00/64876 A1 | 11/2000 |
| WO | 00/64888 A1 | 11/2000 |
| WO | 01/12187 A2 | 2/2001 |
| WO | 01/53298 A1 | 7/2001 |
| WO | 01/83485 A1 | 11/2001 |
| WO | 02/030895 A1 | 4/2002 |
| WO | 02/36590 A1 | 5/2002 |
| WO | 02/072549 A1 | 9/2002 |
| WO | 03/000253 A1 | 1/2003 |
| WO | 03/000684 A1 | 1/2003 |
| WO | 03/031409 A1 | 4/2003 |
| WO | 03/068742 A1 | 8/2003 |
| WO | 03/087087 A2 | 10/2003 |
| WO | 2004/052854 A2 | 6/2004 |

OTHER PUBLICATIONS

Ballantine, J. A., "The Chemistry of Bacteria," *Journal of the Chemical Society Abstracts*, 1957, 2222-2227.

Charlton, Peter, "The status of plasminogen activator inhibitor-1 as a therapeutic target," *Expert Opinion On Investigational Drugs*, May 1997, 6(5), 539-554.

Crandall, D. L. et al., "Characterization and comparative evaluation of a structurally unique PAI-1 inhibitor exhibiting oral in-vivo efficacy," *Journal of Thrombosis and Haemostasis*, Mar. 17, 2004, 2, 1422-1428.

Da Settimo, A. et al., "Reaction of indole derivatives with bromine, substitution, oxidation, and dimerization," J Org Chem, 1970, 35(8):2546-2551.

Delgado et al., Journal of Organic Chemistry (1993), 58(10), pp. 2862-2866.

Dillard R. D. et al., "Indole Inhibitors of Human Nonpancreatic Secretory Phospholipase $A_2$ 1. Indole 3-Acetamides", *Journal of Medicinal Chemistry*, American Chemical Society, 39(26), 5119-5136.

Guzzo, P.R. et al., "Synthesis of a conformationally constrained threonin-valine dipeptide mimetic: design of a potential inhibitor of plasminogen activator inhibitor-1," *Tetrahedron Letters*, 2002 43(1), 41-43.

Hipskind, P. A. et al., "Potent and selective 1,2,3-trisubstituted indole NPY Y-1 antagonists," *J Med Chem*, 1997, 40(23), 3712-3714.

Julia et al., CA 57:49169, 1962.

Malamas, M. S. et al., "Antihyperglycemic activity of new 1,2,4-oxadiazolidine-3,5-diones," *Eur. J. Med. Chem.*, 2001, 36, 31-42.

Malamas, M.S. et al. "Novel benzofuran and benzothiophene biphenyls as inhibitors of protein tyrosine phosphatase 1B with antihyperglycemic properties," *Journal of Medicinal Chemistry*, Apr. 6, 2000, 43(7), 1293-1310.

Moody et al., CA 120:298300, 1994.

U.S. Appl. No. 10/947,711, filed Sep. 23, 2004, Gopalsamy et al.

Aznar, J. et al., "Role of Plasminogen Activator Inhibitor Type 1 in the Pathogenesis of Coronary Artery Diseases," *Haemostasis*, 24: 243-251 (1994).

Biemond, B. J. et al., "Thrombolysis and Reocclusion in Experimental Jugular Vein and Coronary Artery Thrombosis," *Circulation*, 91:1175-1181 (1995).

Carmeliet, P. et al., "Plasminogen Activator Inhibitor—1 Gene-deficient Mice," *Journal of Clinical Investigation*, 92: 2756-2760 (Dec. 1993).

Daci, E. et al., "Mice Lacking the Plasminogen Activator Inhibitor 1 are Protected from Trabecular Bone Loss Induced by Estrogen Deficiency," *Journal of Bone and Mineral Research*, 15(8):1510-1516 (Nov. 8, 2000).

Hamsten, A. et. al., "Plasminogen Activator Inhibitor in Plasma: Risk Factor For Recurrent Myocardial Infarction," *Lancet*, 2: 3-9 (Jul. 4, 1987).

Juhan-Vague, I. et. al., "Deficient t-PA Release and Elevated PA Inhibitor Levels in Patients with Spontaneous or Recurrent Deep Venous Thrombosis," *Thromb Haemost*, 57: 67-72 (1987).

Juhan-Vague, I. et. al., "PAI-1, Obesity, Insulin Resistance and Risk of Cardiovascular Events," *Thromb Haemost*, 78: 656-660 (1997).

Koh, K. et. al., "Effects of Hormone-Replacement Therapy on Fibrinolysis in Postmenopausal Women," *N Engl J Med*, 336(10): 683-690 (Mar. 6, 1997).

Krishnamurti, C. et al., "Plasminogen Activator Inhibitor: A Regulator of Ancrod-Induced Fibrin Deposition in Rabbits," *Blood*, 69(3): 798-803 (Mar. 1987).

Levi, M. et al., "Inhibition of Plasminogen Activator Inhibitor-1 Activity Results in Promotion of Endogenous Thrombolysis and Inhibition of Thrombus Extension in Models of Experimental Thrombosis," *Circulation*, 85, 305, (1992).

Nordt, T. K. et al., "Differential Regulation by Troglitazone of Plasminogen Activator Inhibitor Type 1 in Human Hepatic and Vascular Cells," *Journal of Clinical Endocrinology and Metabolism*, 85(4):1563-1568 (2000).

Reilly, C. et al., "Both Circulating and Clot-Bound Plasminogen Activator-1 Inhibit Endogenous Fibrinolysis in the Rat," *Arteriosclerosis and Thrombosis*, 11(5): 1276-1286 (Sep./Oct. 1991).

Rocha, E. et al., "The Relationship Between Impaired Fibrinolysis and Coronary Heart Disease," *Fibrinolysis*, 8: 294-303 (1994).

Schneiderman, J. et. al., "Increased type 1 plasminogen activator inhibitor gene expression in atherosclerotic human arteries," *Proc Natl Acad Sci* 89: 6998-7002 (Aug. 1992).

Siemens, H. J. et. al., "Course of Molecular Hemostatic Markers During and After Different Surgical Procedures," *J Clin Anesthesia* 11: 622-629 (Dec. 1999).

PYRROLO-NAPHTHYL ACIDS AND METHODS FOR USING THEM

CROSS-REFERENCE TO RELATED APPLICATIONS

This application claims priority to provisional application Ser. No. 60/603,766 filed on Aug. 23, 2004 incorporated herein by reference in its entirety

BACKGROUND

The present invention relates generally to pyrrolo-napthyl acids, such as pyrrolo-5-yl-naphthyl]oxyalkyl-acids, and methods of using them.

The serine protease inhibitor PAI-1 is one of the primary inhibitors of the fibrinolytic system. The fibrinolytic system includes the proenzyme plasminogen, which is converted to the active enzyme, plasmin, by one of two tissue type plasminogen activators, t-PA or u-PA. PAI-1 is the principal physiological inhibitor of t-PA and u-PA. One of plasmin's main functions in the fibrinolytic system is to digest fibrin at the site of vascular injury. The fibrinolytic system, however, is not only responsible for the removal of fibrin from circulation but is also involved in several other biological processes including ovulation, embryogenesis, intima proliferation, angiogenesis, tumorigenesis, and atherosclerosis.

Elevated levels of PAI-1 have been associated with a variety of diseases and conditions including those associated with impairment of the fibrinolytic system. For example, elevated levels of PAI-1 have been implicated in thrombotic diseases, e.g., diseases characterized by formation of a thrombus that obstructs vascular blood flow locally or detaches and embolizes to occlude blood flow downstream. (Krishnamurti, *Blood*, 69, 798 (1987); Reilly, Arteriosclerosis and Thrombosis, 11, 1276 (1991); Carmeliet, *Journal of Clinical Investigation*, 92, 2756 (1993), Rocha, *Fibrinolysis*, 8, 294, 1994; Aznar, *Haemostasis* 24, 243 (1994)). Antibody neutralization of PAI-1 activity resulted in promotion of endogenous thrombolysis and reperfusion (Biemond, *Circulation*, 91, 1175 (1995); Levi, *Circulation* 85, 305, (1992)). Elevated levels of PAI-1 have also been implicated in diseases such as polycystic ovary syndrome (Nordt, *Journal of clinical Endocrinology and Metabolism*, 85, 4, 1563 (2000)), bone loss induced by estrogen deficiency (Daci, *Journal of Bone and Mineral Research*, 15, 8, 1510 (2000)), cystic fibrosis, diabetes, chronic periodontitis, lymphomas, diseases associated with extracellular matrix accumulation, malignancies and diseases associated with neoangiogenesis, inflammatory diseases, vascular damage associated with infections, and diseases associated with increased uPA levels such as breast and ovarian cancer.

In view of the foregoing, there exists a need for inhibitors of PAI-1 activity and methods of using them to modulate PAI-1 expression or activity, for example, in treating disorders associated with elevated PAI-1 levels.

SUMMARY

In one aspect, the present invention relates to pyrrolo-naphthyl acids of the following formula:

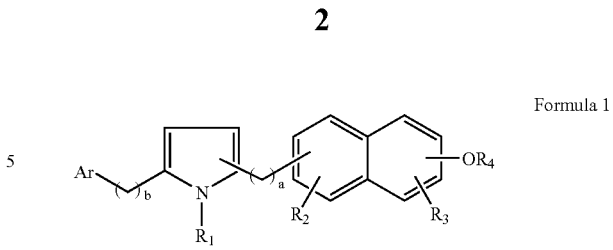

Formula 1 or solvates, hydrates or pharmaceutically acceptable salt or ester forms thereof; wherein:

Ar is aryl or heteroaryl;

$R_1$ is hydrogen, $C_1$–$C_{12}$ alkyl, $C_{6-14}$ aryl, $C_{6-14}$ar($C_{1-6}$) alkyl, —$(CH_2)_p$-heteroaryl, —$(CH_2)_p$—CO-aryl, —$(CH_2)_p$—CO-heteroaryl, —$(CH_2)_p$—CO—$(C_1$–$C_6)$alkyl, $C_2$–$C_7$ alkenyl, $C_2$–$C_7$ alkynyl, or $C_3$–$C_8$ cycloalkyl.

$R_2$ and $R_3$ are independently hydrogen, $C_1$–$C_{12}$ alkyl, $C_{6-14}$ aryl, $C_{6-14}$ar($C_{1-6}$)alkyl, —$(CH_2)_p$-heteroaryl, halogen, $C_1$–$C_6$ alkoxy, aralkyl, alkoxyaryl, nitro, carboxy($C_1$–$C_6$ alkyl), carbamide, carbamate, or $C_3$–$C_8$ cycloalkyl;

$R_4$ is —$CH(R_6)(CH_2)_nR_5$, —$C(CH_3)_2R_6$, —$CH(R_5)(CH_2)_nR_6$, —$CH(R_5)C_6H_4R_6$, —$CH(R_5)C_6H_3(CO_2H)_2$, $CH(R_5)C_6H_2(CO_2H)_3$, or an acid mimic;

$R_5$ is hydrogen, $C_1$–$C_6$ alkyl, $C_6$–$C_{12}$ aryl, aralkyl, $C_3$–$C_8$ cycloalkyl, or —$(CH_2)_n(R_7)$;

$R_6$ is $CO_2H$, tetrazole, or $PO_3H$;

$R_7$ is

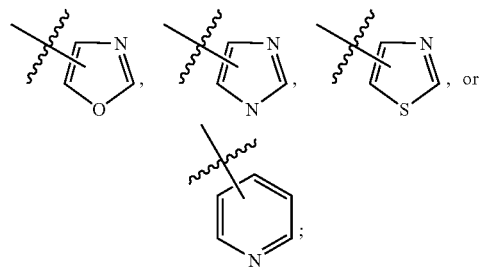

n is from 0 to 6;

p is from 0 to 3;

b is from 0 to 6; and a is from 0 to 6.

The present invention further provides, inter alia, methods of using pyrrolonapthyl acids to, for example, modulate PAI-1 expression and/or activity. In certain methods, a therapeutically effective amount of one or more compounds of the present invention is administered to a subject to treat a PAI-1 related disorder. Examplary methods are those that involve inhibiting PAI-1 activity in the subject, such as that associated with impairment of the fibrinolytic system. In certain embodiments, one or more compounds of the present invention is administered to a subject to treat thrombosis, e.g., venous thrombosis, arterial thrombosis, cerebral thrombosis, and deep vein thrombosis, atrial fibrillation, pulmonary fibrosis, thromboembolic complications of surgery, cardiovascular disease, e.g., myocardial ischemia, atherosclerotic plaque formation, chronic obstructive pulmonary disease, renal fibrosis, polycystic ovary syndrome, Alzheimer's disease, or cancer.

DETAILED DESCRIPTION

A. General Overview

The present invention provides novel compounds that preferably inhibit PAI-1 activity, processes for preparing such compounds, pharmaceutical compositions containing such compounds, and methods for using such compounds, for example, in medical therapies. Preferred compounds have properties that are useful for prevention and/or inhibition of a wide variety of diseases and disorders including those involving the production and/or action of PAI-1. These include disorders resulting from impairment of the fibrinolytic system including, but not limited to, thrombosis, coronary heart disease, renal fibrosis, atherosclerotic plaque formation, pulmonary disease, myocardial ischemia, atrial fibrillation, coagulation syndromes, thromboembolic complications of surgery, peripheral arterial occlusion and pulmonary fibrosis. Other disorders include, but are not limited to, polycystic ovary syndrome, Alzheimer's disease, and cancer.

The terms "alkyl" and "alkylene," as used herein, whether used alone or as part of another group, refer to substituted or unsubstituted aliphatic hydrocarbon chains, the difference being that alkyl groups are monovalent (i.e., terminal) in nature whereas alkylene groups are divalent and typically serve as linkers. Both include, but are not limited to, straight and branched chains containing from 1 to about 12 carbon atoms, preferably 1 to about 6 carbon atoms, unless explicitly specified otherwise. For example, methyl, ethyl, propyl, isopropyl, butyl, i-butyl and t-butyl are encompassed by the term "alkyl." Specifically included within the definition of "alkyl" are those aliphatic hydrocarbon chains that are optionally substituted. Accordingly, the alkyl groups described herein refer to both unsubstituted or substituted groups. Representative optional substituents include, but are not limited to, halogens, —CN, hydroxy, oxo (=O), acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. Preferred substituents include halogens, —CN, —OH, oxo (=O), and amino groups.

The carbon number as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted aliphatic hydrocarbon chain and includes, but is not limited to, straight and branched chains having 2 to about 10 carbon atoms (unless explicitly specified otherwise) and containing at least one double bond. Preferably, the alkenyl moiety has 1 or 2 double bonds. Preferably, the alkenyl moiety has about 2 to about 7 carbon atoms. Such alkenyl moieties can exist in the E or Z conformations and the compounds of this invention include both conformations. Specifically included within the definition of "alkenyl" are those aliphatic hydrocarbon chains that are optionally substituted. Accordingly, the alkenyl groups described herein refer to both unsubstituted or substituted groups. Representative optional substituents include, but are not limited to, halogens, —CN, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. Heteroatoms, such as O or S attached to an alkenyl should not be attached to a carbon atom that is bonded to a double bond. Preferred substituents include halogens, —CN, —OH, and amino groups.

The term "alkynyl", as used herein, whether used alone or as part of another group, refers to a substituted or unsubstituted aliphatic hydrocarbon chain and includes, but is not limited to, straight and branched chains having 2 to about 10 carbon atoms (unless explicitly specified otherwise) and containing at least one triple bond. Preferably, the alkynyl moiety has about 2 to about 7 carbon atoms. In certain embodiments, the alkynyl can contain more than one triple bond and, in such cases, the alkynyl group must contain at least four carbon atoms. Specifically included within the definition of "alkynyl" are those aliphatic hydrocarbon chains that are optionally substituted. Accordingly, the alkynyl groups described herein refer to both unsubstituted or substituted groups. Representative optional substituents include, but are not limited to, halogens, —CN, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. Preferred substituents include halogens, —CN, —OH, and amino groups. Heteroatoms, such as O or S attached to an alkynyl should not be attached to the carbon that is bonded to a triple bond.

The term "cycloalkyl" as used herein, whether alone or as part of another group, refers to a substituted or unsubstituted alicyclic hydrocarbon group having 3 to about 20 carbon atoms (unless explicitly specified otherwise), preferably 3 to about 6 carbon atoms. Specifically included within the definition of "cycloalkyl" are those alicyclic hydrocarbon groups that are optionally substituted. Accordingly, the cycloalkyl groups described herein refer to both unsubstituted or substituted groups. Representative optional substituents include, but are not limited to, hydroxy, oxo (=O), acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl.

The term "aryl", as used herein, whether used alone or as part of another group, is defined as a substituted or unsubstituted aromatic hydrocarbon ring group having 5 to about 50 carbon atoms (unless explicitly specified otherwise) with from about 6 to about 14 carbon atoms being preferred, more preferably from about 6 to about 12 carbon atoms. The "aryl" group can have a single ring or multiple condensed rings. The term "aryl" includes, but is not limited to phenyl, α-naphthyl, β-naphthyl, biphenyl, anthryl, tetrahydronaphthyl, fluorenyl, indanyl, biphenylenyl, and acenaphthenyl. Specifically included within the definition of "aryl" are those aromatic groups that are optionally substituted. Accordingly, the aryl groups (e.g., phenyl, naphthyl, and fluorenyl) described herein refer to both unsubstituted or substituted groups. In representative embodiments of the present invention, the "aryl" groups are optionally substituted with from 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, $C_3$–$C_6$ cycloalkyl, —$(CH_2)_p$—$C_3$–$C_6$ cycloalkyl, $C_1$–$C_3$ perfluoroakyl, $C_1$–$C_3$ perfluoroalkoxy, —$(CH_2)_p$-phenyl, —$O(CH_2)_p$-phenyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. For example, the "aryl" groups can be optionally substituted with from 1 to 3 groups selected from $C_1$–$C_6$ alkyl, $C_1$–$C_6$ alkoxy, hydroxy, $C_3$–$C_6$cycloalkyl, —$(CH_2)_p$—$C_3$–$C_6$ cycloalkyl, halogen, $C_1$–$C_3$ perfluoroalkyl, $C_1$–$C_3$ perfluoroalkoxy, —$(CH_2)_p$-phenyl, and —$O(CH_2)_p$-phenyl In these embodiments, the phenyl group of —$(CH_2)_p$-phenyl and —$O(CH_2)_p$-phenyl can be optionally substituted with, for example, from 1 to 3 groups selected from $C_1$–$C_6$ alkyl, $C_1$–$C_6$ alkoxy, —$(CH_2)_p$-phenyl, halogen, trifluoromethyl or trifluoromethoxy. Preferred aryl groups include phenyl and naphthyl. P is an integer from 0 to 3. Preferred substituents on the aryl groups herein include $C_1$–$C_6$ alkyl, $C_1$–$C_6$ alkoxy, halo, cyano, nitro, trihalomethyl, and $C_1$–$C_6$ thioalkoxy.

As used herein, the term "heteroaryl", whether used alone or as part of another group, is defined as a substituted or unsubstituted aromatic heterocyclic ring system. Heteroaryl groups can have, for example, from about 3 to about 50 carbon atoms (unless explicitly specified otherwise), with from about 4 about 10 being preferred. In some embodiments, heteroaryl groups are aromatic heterocyclic ring systems having 5 to 14 ring atoms and containing carbon atoms and 1, 2, 3 or 4 oxygen, nitrogen or sulfur heteroatoms.

Representative heteroaryl groups are furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzothiophene, benzisoxazole, benzimidazole, N-methylbenzimidazole, azabenzimidazole, indazole, quinazoline, quinoline, and isoquinoline. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Specifically included within the definition of "heteroaryl" are those aromatic groups that are optionally substituted. Accordingly, the heteroaryl groups (e.g., furanyl, thiophenyl, benzofuranyl, benzothiophenyl, indolyl, pyrazolyl, and oxazolyl) described herein refer to both unsubstituted or substituted groups. In representative embodiments of the present invention, the "heteroaryl" groups are optionally substituted with from 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, $C_3$–$C_6$ cycloalkyl, —$(CH_2)_p$—$C_3$–$C_6$ cycloalkyl, $C_1$–$C_3$ perfluoroalkyl, $C_1$–$C_3$ perfluoroalkoxy, —$(CH_2)_p$-phenyl, —$O(CH_2)_p$-phenyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. In some embodiments of the present invention, the "heteroaryl" groups can be optionally substituted with from 1 to 3 groups selected from $C_1$–$C_6$ alkyl, $C_1$–$C_6$ alkoxy, hydroxy, $C_3$–$C_6$ cycloalkyl, —$(CH_2)_p$—$C_3$—$C_6$ cycloalkyl, halogen, $C_1$–$C_3$ perfluoroalky, $C_1$–$C_3$ perfluoroalkoxy, —$(CH_2)_p$-phenyl, and —$O(CH_2)_p$-phenyl. In these embodiments, the phenyl group of —$(CH_2)_p$-phenyl and —$O(CH_2)_p$-phenyl can be optionally substituted with, for example, from 1 to 3 groups selected from $C_1$–$C_6$ alkyl, $C_1$–$C_6$ alkoxy, phenyl, halogen, trifluoromethyl or trifluoromethoxy. P is an integer of from 0 to 3. Preferred heteroaryls of the present invention include substituted and unsubstituted furanyl, thiophenyl, benzofuranyl, benzothiophenyl, indolyl, pyrazolyl, and oxazolyl.

The term "alkoxy" as used herein, refers to the group $R_a$—O— wherein $R_a$ is an alkyl group as defined above. The term "thioalkoxy" as used herein, refers to the group O—$R_a$—S— wherein $R_a$ is an alkyl group as defined above. Specifically included within the definition of "alkoxy" and "thioalkoxy" are those groups that are optionally substituted. Accordingly, the alkoxy and thioalkoxy groups described herein refer to both unsubstituted or substituted groups. Preferred substituents on alkoxy and thioalkoxy groups include halogens, —CN, —OH, and amino groups.

The term "alkoxyaryl" as used herein, refers to the group $R_a$—O-aryl- wherein $R_a$ is an alkyl group as defined above and aryl is as defined above.

The term "arylalkyl" or "aralkyl" refers to the group —$R_a$—$R_b$, where $R_a$ is an alkylene group as defined above, substituted by $R_b$, an aryl group. Preferred aralkyl groups include $C_{6-14}$ar($C_{1-6}$)alkyl groups. Aralkyl groups of the present invention are optionally substituted. For example, in preferred embodiments, the benzyl groups of the present invention are optionally substituted with from 1 to 3 groups selected from $C_1$–$C_6$ alkyl, $C_1$–$C_6$ alkoxy, hydroxy, $C_3$–$C_6$ cycloalkyl, —$(CH_2)_p$—$C_3$–$C_6$ cycloalkyl, halogen, $C_1$–$C_3$ perfluoroalkyl, $C_1$–$C_3$ perfluoroalkoxy, —$(CH_2)_p$-phenyl, and —$O(CH_2)_p$-phenyl. Examples of arylalkyl moieties include, but are not limited to, benzyl, 1-phenylethyl, 2-phenylethyl, 3-phenylpropyl, 2-phenylpropyl and the like The term "perfluoroalkyl", as used herein, whether used alone or as part of another group, refers to a saturated aliphatic hydrocarbon having 1 to 6 carbon atoms and two or more fluorine atoms and includes, but is not limited to, straight or branched chains, such as —$CF_3$, —$CH_2CF_3$, —$CF_2CF_3$ and —$CH(CF_3)_2$.

The term "halogen" or "halo" refers to chlorine, bromine, fluorine, and iodine.

The term "carbamide," as used herein, refers to the group —C(O)NR'R" where R' and R" are independently hydrogen, alkyl, aryl or cycloalkyl as defined herein.

The term "carbamate," as used herein, refers to the group —OC(O)NR'R" where R' and R" are independently hydrogen, alkyl, aryl or cycloalkyl as defined herein.

The term "acyl" refers to a radical of the formula RC(O)—, where R is hydrogen, alkyl, aryl, or cycloalkyl as defined herein. Suitable acyl radicals include formyl, acetyl, propionyl, and the like.

The term "acyloxy" refers to radicals of the formula RC(O)O—, where R is hydrogen, alkyl, aryl or cycloalkyl as defined herein. Suitable acyloxy radicals include $CH_3COO$—, $CH_3CH_2COO$—, benzoyloxy, and the like.

The term "acylamino" refers to radicals of the formula RC(O)NH— where R is hydrogen, alkyl, aryl, or cycloalkyl as defined herein.

The term "aminoacyl" refers to radicals of the formula —$(R)_{0-3}C(O)NH2$ where R is alkylene as previously described.

The term "treating" or "treatment" refers to any indicia of success in amelioration of an injury, pathology, or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluation. "Treating" or "treatment of a PAI-1 related disorder" includes preventing the onset of symptoms in a subject that may be predisposed to a PAI-1 related disorder but does not yet experience or exhibit symptoms of the disorder (prophylactic treatment), inhibiting the symptoms of the disorder (slowing or arresting its development), providing relief from the symptoms or side-effects of the disorder (including palliative treatment), and/or relieving the symptoms of the disorder (causing regression). Accordingly, the term "treating" includes the administration of the compounds or agents of the present invention to a subject to prevent or delay, to alleviate, or to arrest or inhibit development of the symptoms or conditions associated with PAI-1 related disorders, e.g., tumor growth associated with cancer. A skilled medical practitioner will know how to use standard methods to determine whether a patient is suffering from a disease associated with enhanced levels and/or activity of PAI-1, e.g., by examining the patient and determining whether the patient is suffering from a disease known to be associated with elevated PAI-1 levels or activity or by assaying for PAI-1 levels in blood plasma or tissue of the individual suspected of suffering from a PAI-1 related disease and comparing PAI-1 levels in the blood plasma or tissue of the individual suspected of suffering from a PAI-1 related disease to PAI-1 levels in the blood plasma or tissue of a healthy individual. Methods known in the art for the detection of nucleic acids and proteins can be used for determining PAI-1 levels in a subject, e.g., PCR, northern and Southern blots, dot blots, nucleic acid arrays, western blots, immunoassays such as immunoprecipitation, ELISA, proteomics assays, and the like. Increased PAI-1 levels are indicative of disease.

In healthy individuals, PAI-1 is found at low levels in the plasma (e.g., 5–10 ng/mL), but it is elevated significantly in a number of diseases, including, for example, atherosclerosis (Schneiderman J. et. al, *Proc Natl Acad Sci* 89: 6998–7002, 1992) deep vein thrombosis (Juhan-Vague I, et. al, *Thromb Haemost* 57: 67–72, 1987), and non-insulin dependent diabetes mellitus (Juhan-Vague I, et. al, *Thromb Haemost* 78: 565–660, 1997). PAI-1 stabilizes both arterial and venous thrombi, contributing respectively to coronary arterial occlusion in post-myocardial infarction (Hamsten A, et. al. *Lancet* 2:3–9, 1987), and venous thrombosis following post-operative recovery from orthopedic surgery. (Siemens H J, et. al, *J Clin Anesthesia* 11: 622–629, 1999). Plasma PAI-1 is also elevated, for example, in postmenopausal women, and has been proposed to contribute to the increased incidence of cardiovascular disease in this population (Koh K et. al, *N Engl J Med* 336: 683–690, 1997).

The term "PAI-1 related disorder or disease" refers to any disease or condition that is associated with increased or enhanced expression or activity of PAI-1 or increased or enhanced expression or activity of a gene encoding PAI-1. Examples of such increased activity or expression include the following: activity of the protein or expression of the gene encoding the protein is increased above the level of that in normal subjects; activity of the protein or expression of the gene encoding the protein is in an organ, tissue or cell where it is not normally detected in normal subjects (i.e. spatial distribution of the protein or expression of the gene encoding the protein is altered); activity of the protein or expression of the gene encoding the protein is increased when activity of the protein or expression of the gene encoding the protein is present in an organ, tissue or cell for a longer period than in a normal subjects (i.e., duration of activity of the protein or expression of the gene encoding the protein is increased). A normal subject is a subject not suffering from a PAI-1 related disorder or disease.

The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" refers to salts and esters that are pharmaceutically acceptable and have the desired pharmacological properties. Such salts include, for example, salts that can be formed where acidic protons present in the compounds are capable of reacting with inorganic or organic bases. Suitable inorganic salts include, for example, those formed with the alkali metals or alkaline earth metals, e.g. sodium and potassium, magnesium, calcium, and aluminum. Suitable organic salts include, for example, those formed with organic bases such as the amine bases, e.g. ethanolamine, diethanolamine, triethanolamine, tromethamine, N-methylglucamine, and the like. Pharmaceutically acceptable salts can also include acid addition salts formed from the reaction of amine moieties in the parent compound with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g. $C_{1-6}$ alkyl esters.

When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds of the invention can be present in unsalified or unesterified form, or in salified and/or esterified form, and the naming of such compounds is intended to include both the original (unsalified and unesterified) compound and its pharmaceutically acceptable salts and esters. Also, certain compounds can be present in more than one stereoisomeric form, and the naming of such compounds is intended to include all single stereoisomers and all mixtures (whether racemic or otherwise) of such stereoisomers.

The terms "inhibitor," "activator," and "modulator" as used in connection with expression or activity refer to inhibitory, activating, or modulating molecules, respectively. Inhibitors of the present invention include compounds or compositions that inhibit expression of PAI-1 or bind to, partially or totally block stimulation, decrease, prevent, delay activation, inactivate, desensitize, or down regulate the activity of PAI-1. Samples or assays comprising PAI-1 can be treated with a composition of the present invention and compared to control samples without a composition of the present invention. Control samples (untreated with compositions of the present invention) can be assigned a relative activity value of 100%. In certain embodiments, inhibition of PAI-1 is achieved when the activity value relative to the control is about 80% or less, optionally 50% or 25, 10%, 5% or 1%.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the compound.

A "therapeutically effective amount" or "pharmaceutically effective amount" means an amount that, when administered to a subject for treating a disease, is sufficient to effect treatment for that disease.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and formulations of the present invention.

When any variable occurs more than one time in any constituent or in any formula, its definition in each occurrence is independent of its definition at every other occurrence. Combinations of substituents and/or variables are permissible only if such combinations result in stable compounds.

B. Pyrrolo-Naphthyl Acids

As noted above, the compounds of the present invention include those of the following formula:

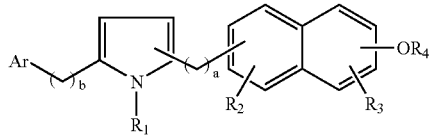

Formula 1 or solvates, hydrates or pharmaceutically acceptable salt or ester forms thereof; wherein:

Ar is aryl or heteroaryl;

$R_1$ is hydrogen, $C_1$–$C_{12}$ alkyl, $C_{6-14}$ aryl, $C_{6-14}$ar($C_{1-6}$) alkyl, —$(CH_2)_p$-heteroaryl, —$(CH_2)_p$—CO-aryl, —$(CH_2)_p$—CO-heteroaryl, —$(CH_2)_p$—CO—$(C_1$–$C_6)$alkyl, arakyl, $C_2$–$C_7$ alkenyl, $C_2$–$C_7$ alkynyl, or $C_3$–$C_8$ cycloalkyl;

$R_2$ and $R_3$ are independently hydrogen, $C_1$–$C_{12}$ alkyl, $C_{6-14}$ aryl, $C_{6-14}$ar($C_{1-6}$)alkyl, —$(CH_2)_p$-heteroaryl, halogen, $C_1$–$C_6$ alkoxy, alkoxyaryl, nitro, carboxy($C_1$–$C_6$ alkyl), carbamide, carbamate, or $C_3$–$C_8$ cycloalkyl;

$R_4$ is —$CH(R_6)(CH_2)_n R_5$, —$C(CH_3)_2 R_6$, —$CH(R_5)(CH_2)_n R_6$, —$CH(R_5)C_6H_4 R_6$, —$CH(R_5)C_6H_3(CO_2H)_2$, $CH(R_5)C_6H_2(CO_2H)_3$, or an acid mimic;

$R_5$ is hydrogen, $C_1$–$C_6$ alkyl, $C_6$–$C_{12}$ aryl, aralkyl, $C_3$–$C_8$ cycloalkyl, or —$(CH_2)_n(R_7)$;

$R_6$ is $CO_2H$, tetrazole, or $PO_3H$;

$R_7$ is

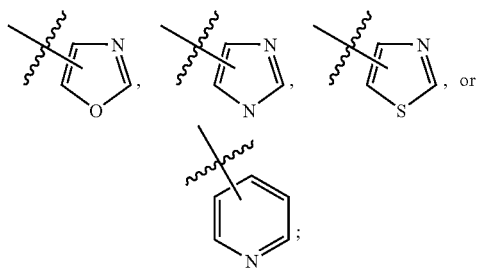

n is from 0 to 6;
p is from 0 to 3;
b is from 0 to 6; and
a is from 0 to 6.

In certain embodiments in the definition of $R_1$, $R_2$ and $R_3$ said $C_1$–$C_{12}$ alkyl is unsubstituted $C_1$–$C_{12}$ alkyl or $C_1$–$C_3$ perfluoroalkyl and said $C_1$–$C_6$ alkoxy is unsubstituted $C_1$–$C_6$ alkoxy or $C_1$–$C_3$ perfluoroalkoxy.

Such pyrrolo-naphthyl acids include the following compounds:

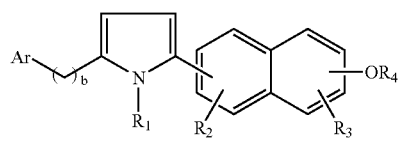

Formula 2

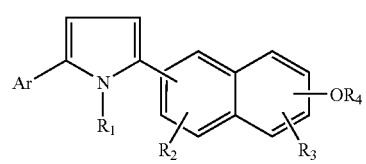

Formula 3

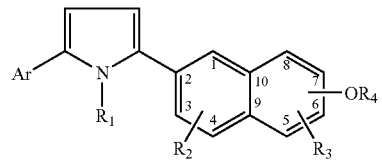

Formula 4

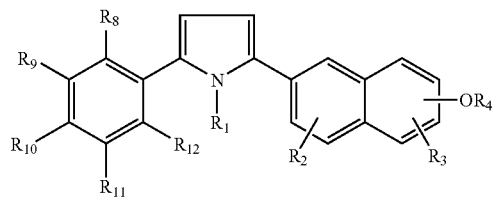

Formula 5 or a solvate, hydrate or pharmaceutically acceptable salt or ester form thereof; wherein:

Ar, $R_1$ to $R_7$, b, n and p are as defined above and $R_8$, $R_9$, $R_{10}$, $R_{11}$ and $R_{12}$ are independently hydrogen, $C_1$–$C_6$ alkyl, $C_1$–$C_6$ alkoxy, hydroxy, $C_3$–$C_6$cycloalkyl, —$(CH_2)_p$—$C_3 C_6$ cycloalkyl, halogen, —$(CH_2)_p$-phenyl, or —$O(CH_2)_p$-phenyl. In certain embodiments said $C_1$–$C_6$ alkyl is unsubstituted $C_1$–$C_6$ alkyl or $C_1$–$C_3$ perfluoroalkyl; said $C_1$–$C_6$ alkoxy is unsubstituted $C_1$–$C_6$ alkoxy or $C_1$–$C_3$ perfluoroalkoxy. In preferred compounds, $R_8$, $R_9$, $R_{10}$, $R_{11}$ and $R_{12}$ are hydrogen.

In exemplary embodiments of Formulas 1, 2, 3, 4 or 5 the definitions have one or more, e.g. all, of the following values:

Ar is aryl or heteroaryl;

$R_1$ is hydrogen, $C_1$–$C_6$ alkyl or —$(CH_2)_p$-phenyl;

$R_2$ and $R_3$ are independently hydrogen, unsubstituted $C_1$–$C_6$ alkyl, phenyl-$(CH_2)_p$—, halogen or $C_1$–$C_3$ perfluoroalkyl;

$R_4$ is —$CHR_5CO_2H$, —$CH_2R_5C_6H_4CO_2H$, —$CH_2R_5C_6H_3(CO_2H)_2$, —$CH_2$-tetrazole or an acid mimic;

$R_5$ is hydrogen, optionally substituted phenyl, or optionally substituted benzyl;

or a solvate, hydrate or pharmaceutically acceptable salt or ester form thereof.

In exemplary embodiments the definitions have one or more, e.g. all, of the following values:

Ar is phenyl, naphthyl, furanyl, thiophenyl, benzofuranyl, benzothiophenyl, indolyl, pyrazolyl, oxazolyl or fluorenyl;

$R_1$ is hydrogen, $C_1$–$C_6$ alkyl or —$(CH_2)_p$-phenyl;

$R_2$ and $R_3$ are independently hydrogen, unsubstituted $C_1$–$C_6$ alkyl, phenyl-$(CH_2)_p$—, halogen or $C_1$–$C_3$ perfluoroalkyl;

$R_4$ is —$CHR_5CO_2H$, —$CHR_5C_6H_4CO_2H$, —$CHR_5C_6H_3(CO_2H)_2$, —$CH_2$tetrazole or an acid mimic;

$R_5$ is hydrogen, optionally substituted phenyl, or optionally substituted benzyl;

or a solvate, hydrate or pharmaceutically acceptable salt or ester form thereof.

In some compounds of the present invention, $OR_4$ is in the 6 position relative to the pyrrole ring (the numbering system used is shown in Formula 4).

Compounds of the present invention also include prodrugs and stereoisomers of formulas 1–5.

In certain exemplary embodiments, $R_1$ is hydrogen, $C_1$–$C_{12}$ alkyl, or —$(CH_2)_p$-phenyl wherein the phenyl ring is optionally substituted with $C_1$–$C_6$ alkyl, $C_1$–$C_6$ alkoxy, halogen, trifluoromethyl, or trifluoromethoxy. In certain compounds, $R_1$ is hydrogen, $C_1$–$C_6$ alkyl or —$(CH_2)_p$-phenyl. For example, in some compounds, $R_1$ is hydrogen, methyl, phenyl, benzyl or 4-trifluoromethylbenzyl.

In some compounds, $R_2$ and $R_3$ are, independently, hydrogen, $C_1$–$C_6$ alkyl, halogen, $C_1$–$C_3$ perfluoroalkyl, or —$(CH_2)_p$-phenyl wherein the phenyl ring is optionally substituted with $C_1$–$C_6$ alkyl, $C_1$–$C_6$ alkoxy, halogen, trifluoromethyl, or trifluoromethoxy. In certain embodiments of the present invention, $R_2$ is hydrogen and $R_3$ is hydrogen or halogen. For example $R_3$ is hydrogen or bromine.

In some compounds, $R_4$ is —$CHR_5CO_2H$, —$CH_2$-tetrazole, —$CH(R_5)C_6H_4CO_2H$, $CH(R_5)C_6H_3(CO_2H)_2$ or an acid mimic. In certain embodiments, $R_4$ is unsubstituted $CH_2COOH$, substituted $CH_2COOH$, —$CH_2$-tetrazole or —$CH(R_5)C_6H_4CO_2H$. In some embodiments, for example $R_4$ is unsubstituted $CH_2COOH$; $CH_2COOH$ wherein the methylene group is substituted with benzyl; —$CH_2$-tetrazole; or —$CH(R_5)C_6H_4CO_2H$.

In some compounds of the present invention, $R_5$ is hydrogen, phenyl or benzyl.

In some exemplary embodiments, Ar is substituted or unsubstituted phenyl, naphthyl, furanyl, thiophenyl, benzofuranyl, benzothiophenyl, indolyl, pyrazolyl, oxazolyl or fluorenyl. In certain embodiments, Ar is a substituted or unsubstituted phenyl.

Exemplary pyrrolo-napthyl acids of the present invention include, but are not limited to, 3-phenyl-2-{[6-(5-phenyl-1H-pyrrol-2-yl)-2-naphthyl]oxy}propanoic acid or a pharmaceutically acceptable salt or ester form thereof; 2-{[6-(1-benzyl-5-phenyl-1H-pyrrol-2-yl)-2naphthyl]oxy}-3-phenylpropanpic acid or a pharmaceutically acceptable salt or ester form thereof; 5-({[6-(5-phenyl-1H-pyrrol-2-yl)-2-naphthyl]oxy}methyl)-1H-tetraazole or a pharmaceutically acceptable salt or ester form thereof; 5-({[6-(1-benzyl-5-phenyl-1H-pyrrol-2-yl)-2-naphthyl]oxy}methyl)-1H-tetraazole or a pharmaceutically acceptable salt or ester form thereof; 5-({[6-(1-methyl-5-phenyl-1H-pyrrol-2-yl)-2-naphthyl]oxy}methyl)-1H-tetraazole or a pharmaceutically acceptable salt or ester form thereof; {[6-(1-benzyl-5-phenyl-1H-pyrrol-2-yl)-2-naphthyl]oxy}acetic acid or a pharmaceutically acceptable salt or ester form thereof; 2-{[6-(1-methyl-5-phenyl-1H-pyrrol-2-yl)-2-naphthyl]oxy}-3-phenylpropanoic acid or a pharmaceutically acceptable salt or ester form thereof; 3-phenyl-2-[(6-{5-phenyl-1-[4-(trifluoromethyl)benzyl]-1H-pyrrol-2-yl}-2-naphthyl)oxy]propanoic acid or a pharmaceutically acceptable salt or ester form thereof; 5-{[(6-{5-phenyl-1-[4-(trifluoromethyl)benzyl]-1H-pyrrol-2-yl}-2-naphthyl)oxy]methyl}-1H-tetraazole or a pharmaceutically acceptable salt or ester form thereof; [(6-{5-phenyl-1-[4-(trifluoromethyl)benzyl]-1H-pyrrol-2-yl}-2-naphthyl)oxy]acetic acid or a pharmaceutically acceptable salt or ester form thereof; 5-({[6-(1,5-diphenyl-1H-pyrrol-2-yl)-2-naphthyl]oxy}methyl)-1H-tetraazole or a pharmaceutically acceptable salt or ester form thereof; {[6-(1,5-diphenyl-1H-pyrrol-2-yl)-2-naphthyl]oxy}acetic acid or a pharmaceutically acceptable salt or ester form thereof; 2-{[6-(1,5-diphenyl-1H-pyrrol-2-yl)-2-naphthyl]oxy}-3-phenylpropanoic acid or a pharmaceutically acceptable salt or ester form thereof, 4-{[(6-{5-phenyl-1-[4-(trifluoromethyl)benzyl]-1H-pyrrol-2-yl}-2-naphthyl)oxy]methyl}benzoic acid or a pharmaceutically acceptable salt or ester form thereof; 4-({[6-(1,5-diphenyl-1H-pyrrol-2-yl)-2-naphthyl]oxy}methyl)benzoic acid or a pharmaceutically acceptable salt or ester form thereof; 4-{[(6-{5-phenyl-1-[4-(trifluoromethyl)benzyl]-1H-pyrrol-2-yl}-2-naphthyl)oxy]methyl}isophthalic acid or a pharmaceutically acceptable salt or ester form thereof; 4-({[6-(5-phenyl-1H-pyrrol-2-yl)-2-naphthyl]oxy}methyl)isophthalic acid or a pharmaceutically acceptable salt or ester form thereof.

The present invention also provides compositions comprising the pyrrolo-naphthyl acids of the present invention, including those compounds of formulas 1–5 or a stereoisomer or pharmaceutically acceptable solvate, hydrate, salt or ester form thereof, and one or more pharmaceutically acceptable carriers, excipients, or diluents. Such compositions include pharmaceutical compositions for treating or controlling disease states or conditions associated with increased PAI-1 activity. In certain embodiments, the compositions comprise mixtures of one or more pyrrolo-naphthyl acids.

Certain of the compounds of formulas 1–5 contain stereogenic carbon atoms or other chiral elements and thus give rise to stereoisomers, including enantiomers and diastereomers. The present invention includes all of the stereoisomers of formulas 1–5, as well as mixtures of the stereoisomers. Throughout this application, the name of the product, where the absolute configuration of an asymmetric center is not indicated, is intended to embrace the individual stereoisomers as well as mixtures of stereoisomers.

Where an enantiomer is preferred, it can, in some embodiments, be provided substantially free of the corresponding enantiomer. Thus, an enantiomer substantially free of the corresponding enantiomer refers to a compound that is isolated or separated via separation techniques or prepared free of the corresponding enantiomer. "Substantially free," as used herein, means that the compound is made up of a significantly greater proportion of one enantiomer. In preferred embodiments, the compound is made up of at least about 90% by weight of a preferred enantiomer. In other embodiments of the invention, the compound is made up of at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein. Methods for the preparation of preferred enantiomers are described, for example, in Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); and Wilen, S. H. Tables of Resolving Agents and Optical Resolutions p. 268 (E. L. Eliel, Ed., Univ. of Notre Dame Press, Notre Dame, Ind. 1972).

Exemplary salt forms of the compounds herein include, but are not limited to, sodium salts and potassium salts. Other exemplary salt forms of these compounds include, but are not limited to, those formed with pharmaceutically acceptable inorganic and organic bases or acids known in the art. The acids include, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable aids when a compound of this invention contains a basic moiety. Salt forms prepared using inorganic bases include hydroxides, carbonates or bicarbonates of the therapeutically acceptable alkali metals or alkaline earth metals, such as sodium potassium, magnesium, calcium and the like. Acceptable organic bases include amines, such as benzylamine, mono-, di- and trialkylamines, preferably those having alkyl groups of from 1 to 6 carbon atoms, more preferably 1 to 3 carbon atoms, such as methylamine, dimethylamine, trimethylamine, ethylamine, diethylamine, triethylamine, mono-, di-, and triethanolamine. Exemplary salts also include alkylene diamines containing up to 6 carbon atoms, such as hexamethylenediamine; cyclic saturated or unsaturated bases containing up to 6 carbon atoms, including pyrrolidine, piperidine, morpholine, piperazine and their N-alkyl and N-hydroxyalkyl derivatives, such as N-methyl-morpholine and N-(2-hydroxyethyl)-piperidine, or pyridine. Quaternary salts can also be formed, such as tetralkyl forms, such as tetramethyl forms, alkyl-alkanol forms, such as methyl-triethanol or trimethyl-monoethanol forms, and cyclic ammonium salt forms, such as N-methylpyridinium, N-methyl-N-(2-hydroxyethyl)-morpholinium, N,N-di-methylmorpholinium, N-methyl-N-(2-hydroxyethyl)-morpholinium, or N,N-dimethyl-piperidinium salt forms. These salt forms can be prepared using the acidic compound(s) of Formulas 1–2 and procedures known in the art.

Exemplary ester forms of the compounds of this invention include, but are not limited to, straight chain alkyl esters having from 1 to 6 carbon atoms or branched chain alkyl groups containing 1 to 6 carbon atoms, including methyl, ethyl, propyl, butyl, 2-methylpropyl and 1,1-dimethylethyl esters, cycloalkyl esters, alkylaryl esters, benzyl esters, and the like. Other exemplary esters include, but are not limited to, those of the formula —COOR$_{13}$ wherein R$_{13}$ is selected from the formula:

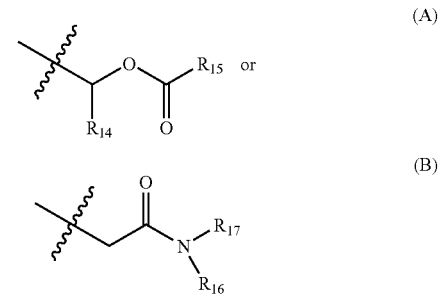

wherein R$_{14}$, R$_{15}$, R$_{16}$, and R$_{17}$ are independently selected from hydrogen, alkyl of from 1 to 10 carbon atoms, aryl of 6 to 12 carbon atoms, arylalkyl of from 6 to 12 carbon atoms; heteroaryl or alkylheteroaryl wherein the heteroaryl ring is bound by an alkyl chain of from 1 to 6 carbon atoms.

Acids and acid mimics, according to the invention, are defined as proton or hydrogen donating groups. Exemplary acid mimics or mimetics of the present invention include pharmaceutically useful carboxylic acids and acid mimics or mimetics known in the art, such as those described in R. Silverman, The Organic Chemistry of Drug Design and Drug Action, Academic Press (1992) and others. Exemplary acid mimics or mimetics include, but are not limited to the following examples, tetrazole, tetronic acid or groups having the formula:

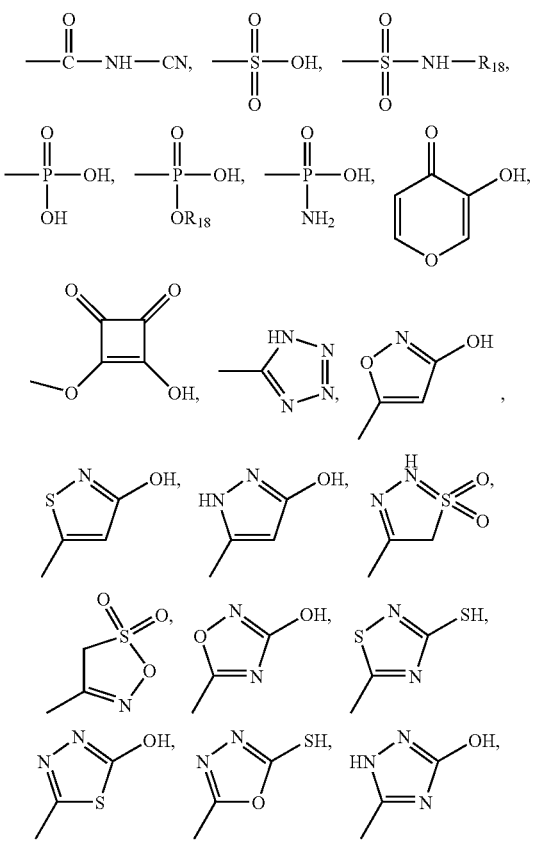

-continued

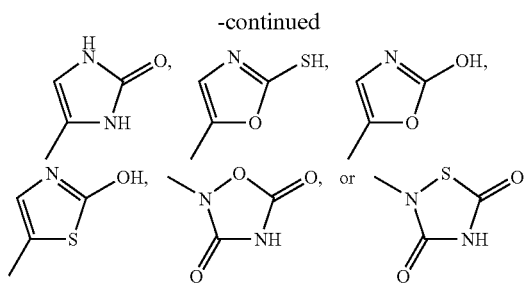

wherein $R_{18}$ is $C_1$–$C_6$ alkyl, $C_2$–$C_6$ alkenyl, $C_3$–$C_6$ cycloalkyl, —$CH_2$—($C_3$–$C_6$ cycloalkyl), $C_3$–$C_6$ cycloalkenyl, —$CH_2$—($C_3$–$C_6$ cycloalkenyl), optionally substituted aryl or heteroaryl groups or optionally substituted aryl ($C_1$–$C_6$)alkyl or heteroaryl($C_1$–$C_6$)alkyl, with the aryl and heteroaryl groups as defined herein.

Preferred compounds of the present invention inhibit PAI-1 activity. Accordingly, the compounds can be used for the treatment, including prevention, inhibition, and/or amelioration of PAI-1 related disorders in a subject, including, for example, in the treatment of noninsulin dependent diabetes mellitus, in the treatment of cardiovascular disease, and in the treatment of thrombotic events including those associated with coronary artery and cerebrovascular disease. Using the methods of the present invention, a skilled medical practitioner will know how to administer the compounds of the present invention, including those represented by formulas 1–5, to a subject suffering from any of the diseases associated with increased PAI-1 activity or expression, e.g., diabetes or cardiovascular disease, in order to effect treatment for that disease.

In one exemplary embodiment, the compounds of the present invention are administered to a subject in order to treat disease processes involving thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary thrombosis, cerebral thrombosis, thromboembolic complications of surgery (such as joint or hip replacement), and peripheral arterial occlusion.

Any disease or condition that is associated with increased PAI-1 activity or expression in a subject can be treated using the compounds of the present invention. Exemplary diseases and conditions include stroke, e.g., stroke associated with or resulting from atrial fibrillation; diseases associated with extracellular matrix accumulation including, but not limited to, renal fibrosis, chronic obstructive pulmonary disease, polycystic ovary syndrome, restenosis, renovascular disease, and organ transplant rejection; diseases associated with neoangiogenesis, including, but not limited to, diabetic retinopathy; Alzheimer's disease, e.g., by increasing or normalizing levels of plasmin concentration in a subject; myelofibrosis with myeloid metaplasia, e.g., by regulating stromal cell hyperplasia and increases in extracellular matrix proteins.

The compounds of the present invention can be used to treat, for example, diabetic nephropathy and renal dialysis associated with nephropathy; malignancies or cancers, including, but not limited to, leukemia, breast cancer and ovarian cancer; tumors, including, but not limited to, liposarcomas and epithelial tumors; septicemia; obesity; insulin resistance; proliferative diseases, including, but not limited to, psoriasis; conditions associated with abnormal coagulation homeostasis; low grade vascular inflammation; cerebrovascular diseases; hypertension; dementia; osteoporosis; arthritis; asthma; heart failure; arrhythmia; angina, including, but not limited to, angina pectoris; atherosclerosis and sequelae; kidney failure; multiple sclerosis; osteoporosis; osteopenia; dementia; peripheral vascular disease; peripheral arterial disease; acute vascular syndromes; microvascular diseases including, but not limited to, nephropathy, neuropathy, retinopathy and nephrotic syndrome; hypertension; Type I and II diabetes and related diseases; hyperglycemia; hyperinsulinemia; malignant lesions; premalignant lesions; gastrointestinal malignancies; coronary heart disease, including, but not limited to, primary and secondary prevention of myocardial infarction, stable and unstable angina, primary prevention of coronary events, and secondary prevention of cardiovascular events; and inflammatory diseases, including, but not limited to, septic shock and the vascular damage associated with infections.

The compounds of the present invention can also be administered to a subject in combination with a second therapeutic agent, including, but not limited to, prothrombolytic, fibrinolytic, and anticoagulant agents, or in conjunction with other therapies, for example, protease inhibitor-containing highly active antiretroviral therapy (HAART) for the treatment of diseases which originate from fibrinolytic impairment and hyper-coagulability of HIV-1 infected patients. In certain embodiments, the compounds of the present invention can be administered in conjunction with and/or following processes or procedures involving maintaining blood vessel patency, including, but not limited to, vascular surgery, vascular graft and stent patency, organ, tissue and cell implantation and transplantation. The compounds of the present invention can also be used for the treatment of blood and blood products used in dialysis, blood storage in the fluid phase, especially ex vivo platelet aggregation. The compounds of the present invention can also be administered to a subject as a hormone replacement agent or to reduce inflammatory markers or C-reactive protein. The compounds can be administered to improve coagulation homeostasis, to improve endothelial function, or as a topical application for wound healing, e.g., the prevention of scarring. The compounds of the present invention can be administered to a subject in order to reduce the risk of undergoing a myocardial revascularization procedure. The present compounds can also be added to human plasma during the analysis of blood chemistry in hospital settings to determine the fibrinolytic capacity thereof. In certain embodiments, the compounds of the present invention can be used as imaging agents for the identification of metastatic cancers.

C. Synthesis Overview

Compounds of the present invention can be prepared by those skilled in the art of organic synthesis employing conventional methods that utilize readily available reagents and starting materials. Representative compounds of the present invention can be prepared using the following synthetic schemes. The skilled practitioner will know how to make use of variants of these process steps, which in themselves are well known in the art. In the following reaction schemes, the substituents are selected from the groups defined above.

Scheme 1

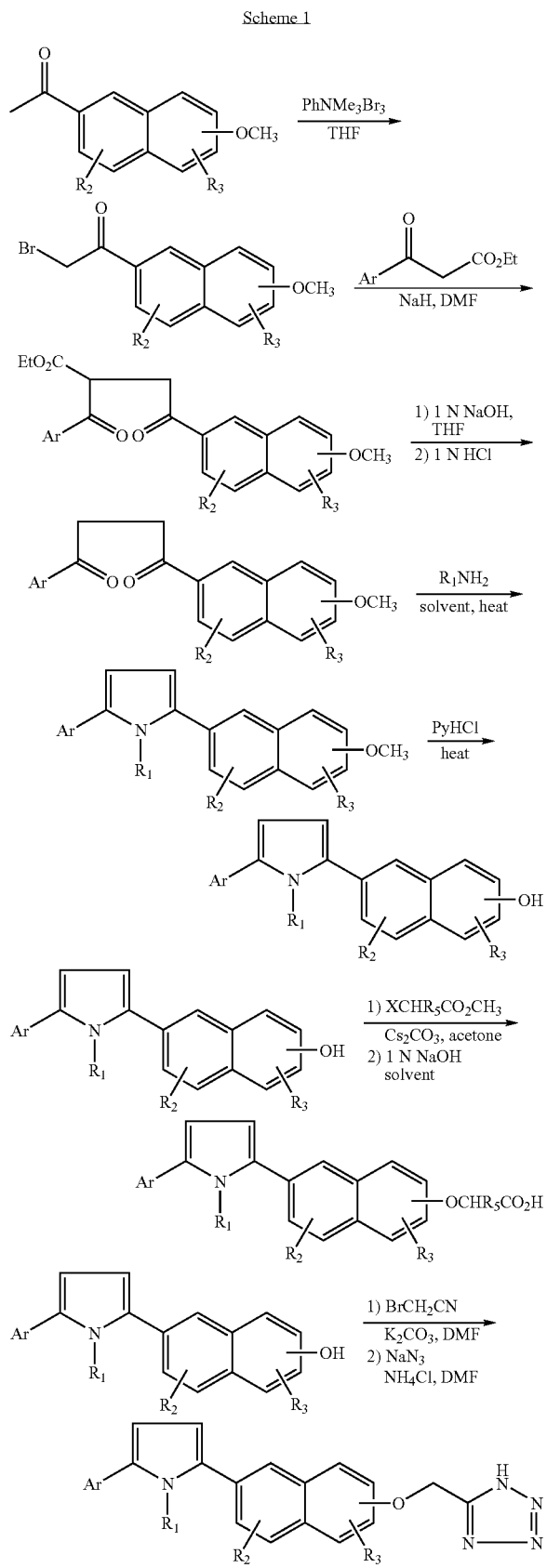

D. Pharmaceutical Compositions

In a preferred embodiment, the compounds of the present invention are formulated as pharmaceuticals to treat diseases associated with increased PAI-1 activity, e.g., by inhibiting PAI-1 activity in a subject.

In general, the compounds of the present invention can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection). Compositions can take the form of tablets, pills, capsules, semisolids, powders, sustained release formulations, solutions, suspensions, emulsions, syrups, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, can be found in such standard references as Alfonso AR: Remington's Pharmaceutical Sciences, 17th ed., Mack Publishing Company, Easton Pa., 1985. Suitable liquid carriers, especially for injectable solutions, include water, aqueous saline solution, aqueous dextrose solution, and glycols. In some embodiments of the present invention, pyrrolo-napthyl acids suitable for use in the practice of this invention will be administered either singly or in combination with at least one other compound of this invention. Pyrrolo-napthyl acids can also be administered with at least one other conventional therapeutic agent for the disease being treated.

Aqueous suspensions of the invention can contain pyrrolo-napthyl acids in admixture with excipients suitable for the manufacture of aqueous suspensions. Such excipients can include, for example, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions can be formulated by suspending a pyrrolo-napthyl acids in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93–102, 1997. The pharmaceutical formulations of the invention can also be in the form of oil-in-water emulsions. The oily phase can be a vegetable oil or a mineral oil, described above, or a mixture of these.

Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of pyrrolo-napthyl acids in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol. The formulations of commends can be presented in unit-dose or multi-dose sealed containers, such as ampules and vials.

Injection solutions and suspensions can be prepared, for example, from sterile powders, granules, and tablets.

Compounds suitable for use in the practice of this invention can be administered orally. The amount of a compound of the present invention in the composition can vary widely depending on the type of composition, size of a unit dosage, kind of excipients, and other factors well known to those of ordinary skill in the art. In general, the final composition can comprise from, for example, 0.000001 percent by weight (% w) to 10% w of the pyrrolo-napthyl acids, preferably 0.00001% w to 1% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient. Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropylmethyl-cellulose or sodium carboxymethyl-cellulose; and gums including arabic and tragacanth; as well as proteins such as gelatin and collagen. If desired, disintegrating or solubilizing agents can be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art The compounds of the present invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, *J. Clin. Pharmacol.* 35:1187–1193, 1995; Tjwa, *Ann. Allergy Asthma Immunol.* 75:107–111, 1995).

The compounds of the present invention can be administered in sustained or controlled release dosage forms (e.g., employing a slow release bioerodable delivery system), including depot injections, osmotic pumps (such as the Alzet implant made by Alza), pills, transdermal and transcutaneous (including electrotransport) patches, and the like, for prolonged administration at a predetermined rate, preferably in unit dosage forms suitable for single administration of precise dosages. The compositions will typically include a conventional pharmaceutical carrier or excipient and a compound of the invention. In addition, these compositions can include other active agents, carriers, adjuvants, and the like.

The compounds of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and the term "composition" is intended to include the active ingredient in combination with an encapsulating material as a formulation, with or without other carriers. For example, the compounds of the present invention can also be delivered as microspheres for slow release in the body. In one embodiment, microspheres can be administered via intradermal injection of drug, which slowly release subcutaneously (see Rao, J. Biomater Sci. Polym. Ed. 7:623–645, 1995; as biodegradable and injectable gel formulations (see, e.g., Gao, *Pharm. Res.* 12:857–863, 1995); or, as microspheres for oral administration (see, e.g., Eyles, *J. Pharm. Pharmacol.* 49:669–674, 1997). Both transdermal and intradermal routes afford constant delivery for weeks or months. Cachets can also be used in the delivery of the compounds of the present invention, e.g., anti-atherosclerotic medicaments.

In another embodiment, the compounds of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compound into the target cells in vivo. (See, e.g., Al-Muhammed, J. Microencapsul. 13:293–306, 1996; Chonn, Curr. Opin. Biotechnol. 6:698–708, 1995; Ostro, Am. J. Hosp. Pharm. 46:1576–1587, 1989).

In other cases, the preferred preparation can be a lyophilized powder in, for example, 1 mM–50 mM histidine, 0.1%–2% sucrose, 2%–7% mannitol at a pH range of 4.5 to 5.5, that is combined with buffer prior to use.

A pharmaceutical composition of the invention can optionally contain, in addition to pyrrolo-napthyl acids, at least one other therapeutic agent useful in the treatment of a disease or condition associated with increased PAI-1 activity.

The pharmaceutical compositions are generally formulated as sterile, substantially isotonic and in full compliance with all Good Manufacturing Practice (GMP) regulations of the U.S. Food and Drug Administration E. Determining Dosage Regimens For treatment purposes, the compositions or compounds disclosed herein can be administered to the subject in a single bolus delivery, via continuous delivery (e.g., continuous transdermal, mucosal, or intravenous delivery) over an extended time period, or in a repeated administration protocol (e.g., by an hourly, daily or weekly, repeated administration protocol). The pharmaceutical formulations of the present invention can be administered, for example, one or more times daily, 3 times per week, or weekly. In an exemplary embodiment of the present invention, the pharmaceutical formulations of the present invention are orally administered once or twice daily.

In this context, a therapeutically effective dosage of the biologically active agent(s) can include repeated doses within a prolonged treatment regimen that will yield clinically significant results to alleviate one or more symptoms or detectable conditions associated with increased PAI-1 activity. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response). In alternative embodiments, an "effective amount" or "therapeutically effective dose" of the biologically active agent(s) will simply inhibit or enhance one or more selected biological activity(ies) correlated with a disease or condition, as set forth above, for either therapeutic or diagnostic purposes.

The actual dosage of biologically active agents will of course vary according to factors such as the extent of exposure and particular status of the subject (e.g., the subject's age, size, fitness, extent of symptoms, susceptibility factors, etc), time and route of administration, as well as other drugs or treatments being administered concurrently. Dosage regimens can be adjusted to provide an optimum prophylactic or therapeutic response. By "therapeutically effective dose" herein is meant a dose that produces effects for which it is administered. More specifically, a therapeutically effective dose of the compound(s) of the invention preferably alleviates symptoms, complications, or biochemical indicia of diseases associated with increased PAI-1 activity. The exact dose will depend on the purpose of the treatment, and will be ascertainable by one skilled in the art using known techniques (see, e.g., Lieberman, Pharmaceutical Dosage Forms (Vols. 1–3, 1992); Lloyd, 1999, The Art, Science, and Technology of Pharmaceutical Compounding; and Pickar, 1999, Dosage Calculations). A therapeutically effective dose is also one in which any toxic or detrimental side effects of the active agent is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

In an exemplary embodiment of the present invention, unit dosage forms of the compounds are prepared for standard administration regimens. In this way, the composition can be subdivided readily into smaller doses at the physicians direction. For example, unit dosages can be made up in packeted powders, vials or ampoules and preferably in capsule or tablet form. The active compound present in these unit dosage forms of the composition can be present in an amount of, for example, from about one gram to about fifteen grams or more, for single or multiple daily administration, according to the particular need of the patient. By initiating the treatment regimen with a minimal daily dose of about one gram, the blood levels of PAI-1 and the patients symptomatic relief analysis can be used to determine whether a larger or smaller dose is indicated. Effective administration of the compounds of this invention can be given at an oral dose of, for example, from about 0.1 mg/kg/day to about 1,000 mg/kg/day. Preferably, administration will be from about 10/mg/kg/day to about 600 mg/kg/day, more preferably from about 25 to about 200 mg/kg/day, and even more preferably from about 50 mg/kg/day to about 100 mg/kg /day. In some embodiments, a daily dosage of from about 1 mg/kg to about 250 mg/kg is provided.

The compounds of the present invention can also be solvated, especially hydrated. Hydration can occur during manufacturing of the compounds or compositions comprising the compounds, or the hydration can occur over time due to the hygroscopic nature of the compounds.

In certain embodiments, the present invention is directed to prodrugs of compounds of formulas 1–5. The term "prodrug," as used herein, means a compound that is convertible in vivo by metabolic means (e.g. by hydrolysis) to a compound of formulas 1–5. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., *Journal of Drug Delivery Reviews*, 8:1–38(1992), Bundgaard, *J. of Pharmaceutical Sciences*, 77:285 et seq. (1988); and Higuchi and Stella (eds.) Prodrugs as Novel Drug Delivery Systems, American Chemical Society (1975).

F. Kits

Pharmaceutical dosage forms comprising a compound of the present invention can be placed in an appropriate container and labeled for treatment of a PAI-1 related disorder, e.g., leukemia. Additionally, another pharmaceutical comprising at least one other therapeutic agent useful in the treatment of the PAI-1 related disorder can be placed in the container as well and labeled for treatment of the indicated disease. For administration of pharmaceutical dosage forms comprising pyrrolo-napthyl acids, such labeling would include, for example, instructions concerning the amount, frequency and method of administration. Similarly, for administration of multiple pharmaceuticals provided in the container, such labeling would include, for example, instructions concerning the amount, frequency and method of administration of each dosage form.

EXAMPLES

Example 1

Synthesis of 3-phenyl-2-{[6-(5-phenyl-1H-pyrrol-2-yl)-2-naphthyl]oxy}propanoic acid Step 1: 2-Bromo-1-(6-methoxy-2-naphthyl)ethanone Phenyltrimethylammoniun tribromide (9.45 g, 25.1 mmol) was added under nitrogen in portions over approximately 2 h to a solution of 1-(6-methoxy-naphthalen-2-yl)-ethanone (5.05 g, 25.2 mmol) in 50 mL of anhydrous THF at room temperature. After the addition the reaction was stirred at room temperature for 0.5 h. and then 250 mL of cold water was added. The solid present was collected by filtration, rinsed with 50 ml, of water and dried under reduced pressure to give 6.66 g of a tan solid. Recrystallization of the solid from isopropyl alcohol gave 2-bromo-1-(6-methoxy-2-(4.07 g, 58%) as a brown solid, mp 109–112° C. Elemental Analysis for $C_{13}H_{11}BrO_2$ Calc'd: C, 55.94; H, 3.97; N, 0.00. Found: C, 56.03; H, 3.94; N, 0.00.

Step 2: Ethyl 2-benzoyl-4-(6-methoxy-2-naphthyl)-4-oxobutanoate

NaH (60%, 1.58 g, 35.8 mmol) was added under nitrogen in 4 equal portions over a 30-minute period to a stirring solution of ethyl benzoylacetate (6.89 g, 35.8 mmol) in 100 mL of anhydrous DMF. After complete addition of the NaH, the mixture was allowed to stir under nitrogen at ambient temperature for 1 hour. After 1 hour, a solution of 2-bromo-1-(6-methoxy-2-naphthyl)ethanone (10.0 g, 35.8 mmol), prepared in the previous step, in 100 mL of anhydrous DMF was added dropwise via a pressure-equalizing addition funnel. Total addition time was approximately 1.5 hours. By TLC analysis (25% EtOAc/Hexane), 30 minutes after addition of the bromoketone was complete, there was no starting material left. The reaction was slowly quenched by the addition of 1N HCl (250 mL). The precipitate was isolated by filtration, rinsed with water and set aside, giving 8.58 g of product. The filtrate was partitioned against EtOAc. The layers were separated and the aqueous layer was extracted with two additional portions of EtOAc. The combined extracts were washed five times with water, dried (MgSO$_4$), filtered and the solvent removed under reduced pressure to give a crude yellow solid. Dissolution of the solid in a minimal amount of methylene chloride followed by precipitation of a solid by the addition of a 2×volume of EtOAc afforded 3.34 g of a white powder. Combination of the like batches gave ethyl 2-benzoyl-4-(6-methoxy-2-naphthyl)-4-oxobutanoate (11.92 g, 85.2%) as an off-white powder, mp 136–137° C. Elemental Analysis for $C_{24}H_{22}O_5$ Calc'd: C, 73.83; H, 5.68; N, 0.00. Found: C, 73.11; H, 5.75; N, 0.00.

Step 3: 1-(6-Methoxy-2-naphthyl)-4-phenylbutane-1,4-dione.

Ethyl 2-benzoyl-4-(6-methoxy-2-naphthyl)-4-oxobutanoate (5.00 g, 12.8 mmol), prepared in the previous step, was dissolved in 300 mL of tetrahydrofuran. After complete dissolution of the ester, 1N NaOH solution (28.2 mL, 28.2 mmol) was added to the THF solution. The mixture was heated to gentle reflux for 24 hours, then allowed to cool back to ambient temperature. The mixture was acidified with 1N hydrochloric acid (105 mL) and allowed to stir for 15 minutes. The THF was then removed under reduced pressure and the residue was partitioned between methylene chloride and 1N HCl. The layers were separated, and the aqueous layer was extracted two times with methylene chloride. The combined extracts were dried (MgSO$_4$), filtered and the solvent removed under reduced pressure. Purification on silica gel (300 g, 200–300 mesh) using methylene chloride as the eluent gave 1-(6-methoxy-2-naphthyl)-4-phenylbutane-1,4-dione as a white solid (1.64 g, 40%), mp 163.5–164.5° C. Elemental Analysis for $C_{21}H_{18}O_3$ Calc'd: C, 79.23; H, 5.70; N, 0.00. Found: C, 79.25; H, 5.70; N, 0.00.

Step 4: 2-(6-Methoxy-2-naphthyl)-5-phenyl-1H-pyrrole.

A mixture of 1-(6-methoxy-2-naphthyl)-4-phenylbutane-1,4-dione (1.00 g, 3.14 mmol), prepared in the previous step, ammonium acetate (12.1 g, 157 mmol) and acetic acid (100 mL) was heated to 100° C. under a nitrogen atmosphere for three hours. The mixture was cooled to ambient temperature, and the precipitate was isolated by filtration to give 2-(6-methoxy-2-naphthyl)-5-phenyl-1H-pyrrole as a white solid (0.86 g, 91%), mp 208.5–209.5° C. Elemental Analysis for $C_{21}H_{17}NO$ Calc'd: C, 84.25; H, 5.72; N, 4.68. Found: C, 84.25; H, 5.77; N, 4.56.

Step 5: 6-(5-Phenyl-1H-pyrrol-2-yl)-2-naphthol.

A mixture of 2-(6-methoxy-2-naphthyl)-5-phenyl-1H-pyrrole (0.72 g, 2.4 mmol), prepared in the previous step, and pyridine hydrochloride (7.2 g) was heated at 200° C. under a nitrogen atmosphere for 1 hour. The mixture was cooled to ambient temperature and the solids were dissolved in 1N HCl (150 mL). The mixture was extracted three times with methylene chloride. The combined extracts were washed one time with water, dried (MgSO$_4$), filtered and the solvent removed under reduced pressure to give 6-(5-phenyl-1H-pyrrol-2-yl)-2-naphthol as a grayish solid (0.65 g, 95%), mp 209.5–210.5 Elemental Analysis for $C_{20}H_{15}NO$ Calc'd: C, 84.19; H, 5.30; N, 4.91. Found: C, 83.38; H, 5.38; N, 4.67.

Step 6: Methyl 3-phenyl-2-{[6-(5-phenyl-1H-pyrrol-2-yl)-2-naphthyl]oxy}propanoate.

A mixture of 6-(5-phenyl-1H-pyrrol-2-yl)-2-naphthol (0.300 g, 1.05 mmol), prepared in the previous step, 3-phenyl-2-trifluoromethanesulfonyloxypropionic acid methyl ester (0.492 g, 1.58 mmol) and cesium carbonate (0.685 g, 2.10 mmol) in acetone (50 mL) was stirred under nitrogen at ambient temperature overnight. The acetone was removed under reduced pressure and the residue partitioned between EtOAc and water. The layers were separated and the aqueous layer was extracted two times with EtOAc. The combined extracts were dried (MgSO$_4$), filtered and the solvent removed under reduced pressure. Purification on a Biotage FlashElute™ system with a KP-Sil Flash 40L column (120 g Silica Gel, 60 Å) using 25% to 60% methylene chloride in hexane as the eluent gave methyl 3-phenyl-2-{[6-(5-phenyl-1H-pyrrol-2-yl)-2-naphthyl]oxy}propanoate as a grayish solid (0.447 g, 95%), mp 140–141° C. Elemental Analysis for $C_{30}H_{25}NO_3$ Calc'd: C, 80.51; H, 5.63; N, 3.13. Found: C, 80.26; H, 5.70; N, 2.94.

Step 7: 3-Phenyl-2-{[6-(5-phenyl-1H-pyrrol-2-yl)-2-naphthyl]oxy}propanoic acid.

A mixture of methyl 3-phenyl-2-{[6-(5-phenyl-1H-pyrrol-2-yl)-2-naphthyl]oxy}propanoate (0.25 g, 0.56 mmol), prepared in the previous step, and 1N NaOH (1.1 mL, 1.1 mmol) in THF (25 mL) was stirred under nitrogen at ambient temperature overnight. By TLC analysis, starting material was still present. The mixture was heated to 60° C. for two hours, at which time no starting material remained. The mixture was cooled to ambient temperature, acidified with 1N HCl (2 mL) and the volatiles were removed under reduced pressure (without the application of heat). The residue was slurried with water, the solids filtered and washed with water. The solids were dissolved in methylene chloride, the solution dried (MgSO$_4$), filtered and the solvent removed under reduced pressure to give the title compound as an off-white solid (0.22 g, 90%), mp 176–178° C. Elemental Analysis for $C_{29}H_{23}NO_3$ Calc'd: C, 80.35; H, 5.35; N, 3.23. Found: C, 79.19; H, 5.31; N, 2.97.

Example 2

Synthesis of 2-{[6-(1-benzyl-5-phenyl-1H-pyrrol-2-yl)-2-naphthyl]oxy}-3-phenylpropanoic acid Step 1: 1-Benzyl-2-(6-methoxy-2-naphthyl)-5-phenyl-1H-pyrrole.

In a similar manner as described in step 4 of Example 1, the title compound was prepared from 1-(6-methoxy-2-naphthyl)-4-phenylbutane-1,4-dione (0.300 g, 0.942 mmol), prepared in step 3 of Example 1, and benzyl amine (0.121 g, 1.13 mmol). The crude material was dissolved in methylene chloride and filtered through silica gel (95 g, 200–300 mesh). The solvent was removed under reduced pressure to give 1-benzyl-2-(6-methoxy-2-naphthyl)-5-phenyl-1H-pyrrole as a white solid (0.32 g, 87%), mp 152–153° C. Elemental Analysis for $C_{28}H_{23}NO$ Calc'd: C, 86.34; H, 5.95; N, 3.60. Found: C, 85.46; H, 6.06; N, 3.58.

Step 2: 6-(1-Benzyl-5-phenyl-1H-pyrrol-2-yl)-2-naphthol.

In a similar manner as described in step 5 of Example 1, the title compound was prepared from 1-benzyl-2-(6-methoxy-2-naphthyl)-5-phenyl-1H-pyrrole (0.22 g, 0.56 mmol), prepared in the previous step, and pyridine hydrochloride (15 g) heated to 180° C. under nitrogen for 3 hours. Purification on a Biotage FlashElute™ system with a KP-Sil Flash 40+M column (90 g Silica Gel, 60 Å) using methylene chloride as the eluent gave 6-(1-benzyl-5-phenyl-1H-pyrrol-2-yl)-2-naphthol a grayish solid (0.155 g, 73%), mp 153–154° C. Elemental Analysis for $C_{27}H_{21}NO$ Calc'd: C, 86.37; H, 5.64; N, 3.73. Found: C, 85.95; H, 5.86; N, 3.59.

Step 3: Methyl 2-{[6-(1-benzyl-5-phenyl-1H-pyrrol-2-yl)-2-naphthyl]oxy}-3-phenylpropanoate.

In a similar manner as described in step 6 of Example 1, the title compound was prepared from 6-(1-benzyl-5-phenyl-1H-pyrrol-2-yl)-2-naphthol (0.140 g, 0.373 mmol), prepared in the previous step, 3-phenyl-2-trifluoromethanesulfonyloxypropionic acid methyl ester (0.175 g, 0.560 mmol) and cesium carbonate (0.243 g, 0.746 mmol). Purification on a Biotage FlashElute™ system with a KP-Sil Flash 40+M column (90 g Silica Gel, 60 Å) using 20% to 50% methylene chloride in hexane as the eluent gave methyl 2-{[6-(1-benzyl-5-phenyl-1H-pyrrol-2-yl)-2-naphthyl]oxy}-3-phenylpropanoate as a white solid (0.175 g, 88%), mp 57–62° C. Elemental Analysis for $C_{37}H_{31}NO_3$ Calc'd: C, 82.66; H, 5.81; N, 2.61. Found: C, 82.39; H, 5.88; N, 2.46.

Step 4: 2-{[6-(1-Benzyl-5-phenyl-1H-pyrrol-2-yl)-2-naphthyl]oxy}-3-phenylpropanoic acid.

In a similar manner as described in step 7 of Example 1, the title compound was prepared from methyl 2-{[6-(1-benzyl-5-phenyl-1H-pyrrol-2-yl)-2-naphthyl]oxy}-3-phenylpropanoate (0.145 g, 0.270 mmol), prepared in the previous step, and the addition of water (3 mL) to the reaction mixture. After the volatiles were removed under reduced pressure, the residue was partitioned between water and methylene chloride. The layers were separated and the aqueous layer was extracted one time with methylene chloride. The combined extracts were dried (MgSO$_4$), filtered and the solvent removed under reduced pressure to give the title compound as an off-white solid (0.127 g, 90%), mp 70–80° C. Elemental Analysis for $C_{36}H_{29}NO_3 \cdot 0.48\ H_2O$ Calc'd: C, 81.23; H, 5.67; N, 2.63. Found: C, 80.67; H 6.28; N, 2.36.

Example 3

Synthesis of 5-({[6-(5-phenyl-1H-pyrrol-2-yl)-2-naphthyl]oxy}methyl)-1H-tetraazole Step 1: {[6-(5-Phenyl-1H-pyrrol-2-yl)-2-naphthyl]oxy}acetonitrile.

In a similar manner as described in step 6 of Example 1, the title compound was prepared from 6-(5-phenyl-1H-pyrrol-2-yl)-2-naphthol (0.285 g, 1.00 mmol), prepared in step 5 of Example 1, bromoacetonitrile (0.144 g, 1.20 mmol) and cesium carbonate (1.63 g, 5.00 mmol) with the exception that the reaction was complete after 2 hours at ambient temperature. The isolated tan solids (0.323 g, 100%) were used without further purification, mp 141.5–142.5° C.

Elemental Analysis for $C_{22}H_{16}N_2O$ Calc'd: C, 81.46; H, 4.97; N, 8.64. Found: C, 80.37; H, 4.93; N, Step 2: 5-({[6-(5-Phenyl-1H-pyrrol-2-yl)-2-naphthyl]oxy}methyl)-1H-tetraazole.

A mixture of {[6-(5-phenyl-1H-pyrrol-2-yl)-2-naphthyl]oxy}acetonitrile (0.20 g, 0.62 mmol), prepared in the previous step, ammonium chloride (0.12 g, 1.85 mmol) and sodium azide (0.099 g, 1.85 mmol) in DMIF (10 mL) was heated at 100° C. under nitrogen for 5 hours. After cooling to ambient temperature, TLC analysis showed that starting material remained. An additional portion each of ammonium chloride and sodium azide was added, and the mixture was again heated at 100° C. for 4 hours, at which time no starting material remained. The mixture was cooled to ambient temperature, acidified with 1N HCl (5 mL) and diluted with water (20 mL). The precipitated solids were isolated by vacuum filtration to give the title compound as a gray solid (0.202 g, 89%), mp 237–240° C. (dec). Elemental Analysis for $C_{22}H_{17}N_5O \cdot 0.55\ H_2O \cdot 0.11\ C_3H_7NO$ Calc'd: C, 69.60; H, 4.94; N, 18.57. Found: C, 69.71; H, 4.64; N, 18.61.

Example 4

Synthesis of 5-({[6-(1-benzyl-5-phenyl-1H-pyrrol-2-yl)-2-naphthyl]oxy}methyl)-1H-tetraazole Step 1: {[6-(1-Benzyl-5-phenyl-1H-pyrrol-2-yl)-2-naphthyl]oxy}acetonitrile.

In a similar manner as described in step 1 of Example 3, the title compound was prepared from 6-(1-benzyl-5-phenyl-1H-pyrrol-2-yl)-2-naphthol (0.250 g, 0.665 mmol), prepared in step 2 of Example 2, bromoacetonitrile (0.096 g, 0.80 mmol) and cesium carbonate (1.08 g, 3.33 mmol) with the exception that the reaction was complete after 70 minutes at ambient temperature. The crude material was dissolved in methylene chloride and filtered through silica gel (45 g, 200–300 mesh). The solvent was removed under reduced pressure to give {[6-(1-benzyl-5-phenyl-1H-pyrrol-2-yl)-2-naphthyl]oxy}acetonitrile as a beige solid (0.276 g, 100%), mp 156–157° C. Elemental Analysis for $C_{29}H_{22}N_2O$ Calc'd: C, 84.03; H, 5.35; N, 6.76. Found: C, 83.15; H, 5.46; N, 6.54.

Step 2: 5-({[6-(1-Benzyl-5-phenyl-1H-pyrrol-2-yl)-2-naphthyl]oxy}methyl)-1H-tetraazole.

In a similar manner as described in step 2 of Example 3, the title compound was prepared from {[6-(1-benzyl-5-phenyl-1H-pyrrol-2-yl)-2-naphthyl]oxy}acetonitrile (0.20 g, 48 mmol), prepared in the previous step, ammonium chloride (0.077 g, 1.44 mmol) and sodium azide (0.094 g, 1.44 mmol) in DMF (10 mL). The solids were isolated by vacuum filtration and dissolved in methylene chloride. The organic solution was dried (MgSO$_4$), filtered and the solvent removed under reduced pressure to give 5-({[6-(1-benzyl-5-phenyl-1H-pyrrol-2-yl)-2-naphthyl]oxy}methyl)-1H-tetraazole as an amorphous beige solid (0.203 g, 92%), mp 190–200° C. (dec). Elemental Analysis for $C_{29}H_{23}N_5O \cdot 0.49\ H_2O \cdot 0.21\ C_3H_7NO$ Calc'd: C, 73.90; H, 5.32; N, 15.15. Found: C, 73.05, H, 5.25; N, 15.03.

Example 5

Synthesis of 5-({[6-(1-methyl-5-phenyl-1H-pyrrol-2-yl)-2-naphthyl]oxy}methyl)-1H-tetraazole Step 1: 2-(6-Methoxy-2-naphthyl)-1-methyl-5-phenyl-1H-pyrrole.

In a similar manner as described in step 4 of Example 1, the title compound was prepared from 1-(6-methoxy-2-naphthyl)-4-phenylbutane-1,4-dione (3.00 g, 9.42 mmol), prepared in step 3 of Example 1, and methyl amine (8 M solution in EtOH, 100 mL, 800 mmol). Isolation of the solids by vacuum filtration gave 2-(6-methoxy-2-naphthyl)-1-methyl-5-phenyl-1H-pyrrole as a white solid (2.5 g, 85%), mp 197–198° C. Elemental Analysis for $C_{22}H_{19}NO$ Calc'd: C, 84.31; H, 6.11; N, 4.47. Found: C, 84.47; H, 6.08; N, 4.41.

Step 2: 6-(1-Methyl-5-phenyl-1H-pyrrol-2-yl)-2-naphthol.

In a similar manner as described in step 5 of Example 1, the title compound was prepared from 2-(6-methoxy-2-naphthyl)-1-methyl-5-ohenyl-1H-pyrrol (2.3 g, 7.3 mmol), prepared in the previous step, and pyridine hydrochloride (60 g) heated at 200° C. for 3 hours under a nitrogen atmosphere. The crude material was dissolved in EtOAc and filtered through silica gel (95 g, 200–300 mesh). The solvent was removed under reduced pressure to give 6-(1-methyl-5-phenyl-1H-pyrrol-2-yl)-2-naphthol as a tan solid (2.0 g, 91%), mp 230–231° C. Elemental Analysis for $C_{21}H_{17}NO$. Calc'd: C, 84.25; H, 5.72; N, 4.68. Found: C, 84.24; H, 5.76; N, 4.61.

Step 3: {[6-(1-Methyl-5-phenyl-1H-pyrrol-2-yl)-2-naphthyl]oxy}acetonitrile.

In a similar manner as described in step 1 of Example 4, the title compound was prepared from 6-(1-methyl-5-phenyl-1H-pyrrol-2-yl)-2-naphthol (0.45 g, 1.5 mmol), prepared in the previous step, bromoacetonitrile (0.216 g, 1.8 mmol) and cesium carbonate (2.45 g, 7.52 mmol) with the exception that the reaction was complete after 100 minutes at ambient temperature. The crude material was dissolved in methylene chloride and filtered through silica gel (45 g, 200–300 mesh). The solvent was removed under reduced pressure to give {[6-(1-methyl-5-phenyl-1H-pyrrol-2-yl)-2-naphthyl]oxy}acetonitrile as an off-white solid (0.494 g, 97%), mp 191.5–192.5° C. Elemental Analysis for $C_{23}H_{18}N_2O$ Calc'd: C, 81.63; H, 5.36; N, 8.28. Found: C, 81.06; H, 5.14; N, 8.04.

Step 4: 5-({[6-(1-Methyl-5-phenyl-1H-pyrrol-2-yl)-2-naphthyl]oxy}methyl)-1H-tetraazole.

In a similar manner as described in step 2 of Example 3, the title compound was prepared from {[6-(1-methyl-5-phenyl-1H-pyrrol-2-yl)-2-naphthyl]oxy}acetonitrile (0.20 g, 0.48 mmol), prepared in the previous step, ammonium chloride (0.077 g, 1.44 mmol) and sodium azide (0.094 g, 1.44 mmol) in DMF (10 mL). The precipitated solids were isolated by vacuum filtration to give 5-({[6-(1-methyl-5-phenyl-1H-pyrrol-2-yl)-2-naphthyl]oxy}methyl)-1H-tetraazole. as a white solid (0.228 g, 81%), mp 231–233° C. (dec). Elemental Analysis for $C_{23}H_{19}N_5O \cdot 0.34\ H_2O \cdot 0.07\ C_3H_7NO$ Calc'd: C, 70.99; H, 5.18; N, 18.08. Found: C, 70.84; H, 5.07; N, 18.18.

Example 6

Synthesis of {[6-(1-benzyl-5-phenyl-1H-pyrrol-2-yl)-2-naphthyl]oxy}acetic acid Step 1: Methyl {[6-(1-benzyl-5-phenyl-1H-pyrrol-2-yl)-2-naphthyl]oxy}acetate.

In a similar manner as described in step 1 of Example 4, the title compound was prepared from 6-(1-benzyl-5-phenyl-1H-pyrrol-2-yl)-2-naphthol (0.250 g, 0.665 mmol), prepared in step 2 of Example 2, methyl bromoacetate (0.122 g, 0.797 mmol) and cesium carbonate (1.08 g, 3.33 mmol). The isolated tan amorphous solid (0.298 g, 100%) was used without further purification, mp 101–102° C. Elemental Analysis for $C_{30}H_{25}NO_3$ Calc'd: C, 80.51; H, 5.63; N, 3.13. Found: C, 79.81; H, 5.60; N, 2.83.

Step 2: {[6-(1-Benzyl-5-phenyl-1H-pyrrol-2-yl)-2-naphthyl]oxy}acetic acid.

A mixture of methyl {[6-(1-benzyl-5-phenyl-1H-pyrrol-2-yl)-2-naphthyl]oxy}acetate (0.250 g, 0.559 mmol), prepared in the previous step, and 1N NaOH (0.84 mL, 0.84 mmol) in 1:1:1 THF:MeOH:water (30 mL) was stirred at ambient temperature for 10 minutes. The volatiles were removed under reduced pressure (without the application of heat). The residue was partitioned between 0.1N HCl and EtOAc. The layers were separated and the aqueous layer was extracted one time with EtOAc. The combined extracts were dried ($MgSO_4$), filtered and the solvent removed under reduced pressure to give the title compound as a pale-yellow solid (0.23 g, 95%), mp 171–172° C. Elemental Analysis for $C_{29}H_{23}NO_3$.0.17 $H_2O$ Calc'd: C, 79.79; H, 5.39; N, 3.21. Found: C, 79.88; H, 5.37; N, 2.96.

Example 7

Synthesis of 2-{[6-(1-methyl-5-phenyl-1H-pyrrol-2-yl)-2-naphthyl]oxy}-3-phenylpropanoic acid Step 1: Methyl 2-{[6-(1-methyl-5-phenyl-1H-pyrrol-2-yl)-2-naphthyl]oxy}-3-phenylpropanoate.

In a similar manner as described in step 6 of Example 1, the title compound was prepared from 6-(1-methyl-5-phenyl-1H-pyrrol-2-yl)-2-naphthol (0.300 g, 1.00 mmol), prepared in step 2 of Example 5, 3-phenyl-2-trifluoromethanesulfonyloxypropionic acid methyl ester (0.469 g, 1.50 mmol) and cesium carbonate (0.653 g, 2.00 mmol) with the exception that this reaction was complete after 4 hours at ambient temperature. Purification on a Biotage Horizon™ system with a KP-Sil Flash 40+M column (100 g Silica Gel, 60 Å) using 25% to 55% methylene chloride in hexane as the eluent gave methyl 2-{[6-(1-methyl-5-phenyl-1H-pyrrol-2-yl)-2-naphthyl]oxy}-3-phenylpropanoate as a white solid (0.437 g, 94%), mp 117–118° C. Elemental Analysis for $C_{31}H_{27}NO_3$ Calc'd: C, 80.67; H, 5.90; N, 3.03. Found: C, 80.35; H, 6.16; N, 2.91.

Step 2: 2-{[6-(1-Methyl-5-phenyl-1H-pyrrol-2-yl)-2-naphthyl]oxy}-3-phenylpropanoic acid.

In a similar manner as described in step 2 of Example 6, the title compound was prepared from methyl 2-{[6-(1-methyl-5-phenyl-1H-pyrrol-2-yl)-2-naphthyl]oxy}-3-phenylpropanoate (0.200 g, 0.433 mmol), prepared in the previous step, and 1N NaOH (0.65 mL, 0.65 mmol) in 1.5:1.5:1 THF:MeOH:water (40 mL) with the exception that this reaction was complete after 18 hours (overnight) at ambient temperature. The title compound was isolated as a pale-yellow solid (0.194 g, 100%) and used without further purification, mp 171–173° C. Elemental Analysis for $C_{30}H_{25}NO_3$.0.05 $H_2O$ Calc'd: C, 80.35; H, 5.64; N, 3.12. Found: C, 80.38; H, 5.67; N, 3.00.

Example 8

Synthesis of 3-phenyl-2-[(6-{5-phenyl-1-[4-(trifluoromethyl)benzyl]-1H-pyrrol-2-yl}2-naphthyl)oxy] propanoic acid Step 1: 2-(6-Methoxy-2-naphthyl)-5-phenyl-1-[4-(trifluoromethyl)benzyl]-1H-pyrrole.

In a similar manner as described in step 4 of Example 1, the title compound was prepared from 1-(6-methoxy-2-naphthyl)-4-phenylbutane-1,4-dione (0.300 g, 0.942 mmol), prepared in step 3 of Example 1, and trifluoromethylbenzyl amine (0.121 g, 1.13 mmol) with the exception that this reaction required 4 hours of heating at 125° C. The crude material was isolated by removal of the acetic acid under reduced pressure. The crude material was dissolved in 50% methylene chloride in hexane and filtered through silica gel (45 g, 200–300 mesh). The solvent was removed under reduced pressure to give 2-(6-methoxy-2-naphthyl)-5-phenyl-1-[4-(trifluoromethyl)benzyl]-1H-pyrrole as an off-white amorphous solid (2.4 g, 83%), mp 94–97° C. Elemental Analysis for $C_{29}H_{22}F_3NO$ Calc'd: C, 76.14; H, 4.85; N, 3.06. Found: C, 76.56; H, 5.58; N, 2.82.

Step 2: 6-{5-Phenyl-1-[4-(trifluoromethyl)benzyl]-1H-pyrrol-2-yl}-2-naphthol.

In a similar manner as described in step 5 of Example 1, the title compound was prepared from 2-(6-methoxy-2-naphthyl)-5-phenyl-1-[4-(trifluoromethyl)benzyl]-1H-pyrrole (0.70 g, 1.5 mmol), prepared in the previous step, and pyridine hydrochloride (7 g) heated to 165° C. under nitrogen for 12 hours. Purification on a Biotage Horizon™ system with a KP-Sil Flash 40+M column (100 g Silica Gel, 60 Å) using 50% to 90% methylene chloride in hexane as the eluent gave 6-{5-phenyl-1-[4-(trifluoromethyl)benzyl]-1H-pyrrol-2-yl}-2-naphthol as a reddish-brown amorphous solid (0.52 g, 77%), mp 63–66° C. Elemental Analysis for $C_{28}H_{20}F_3NO$ Calc'd: C, 75.84; H, 4.55; N, 3.16. Found: C, 75.18; H, 4.41; N, 3.13.

Step 3: Methyl 3-phenyl-2-[(6-{5-phenyl-1-[4-(trifluoromethyl)benzyl]-1H-pyrrol-2-yl}-2-naphthyl)oxy]propanoate.

In a similar manner as described in step 1 of Example 7, the title compound was prepared from 6-{5-phenyl-1-[4-(trifluoromethyl)benzyl]-1H-pyrrol-2-yl}-2-naphthol (0.300 g, 0.676 mmol), prepared in the previous step, 3-phenyl-2-trifluoromethanesulfonyloxypropionic acid methyl ester (0.317 g, 1.02 mmol) and cesium carbonate (0.441 g, 1.35 mmol). Purification on a Biotage Horizon™ system with a KP-Sil Flash 40+M column (100 g Silica Gel, 60 Å) using 25% to 65% methylene chloride in hexane as the eluent gave methyl 3-phenyl-2-[(6-{5-phenyl-1-[4-(trifluoromethyl)benzyl]-1H-pyrrol-2-yl}-2-naphthyl)oxy]propanoate as an off-white amorphous solid (0.367 g, 90%), mp 50–55° C. Elemental Analysis for $C_{38}H_{30}F_3NO_3$ Calc'd: C, 75.36; H, 4.99; N, 2.31. Found: C, 75.24; H, 5.16; N, 2.22.

Step 4: 3-Phenyl-2-[(6-{5-phenyl-1-[4-(trifluoromethyl)benzyl]-1H-pyrrol-2-yl}-2-naphthyl)oxy]propanoic acid.

In a similar manner as described in step 2 of Example 6, the title compound was prepared from methyl 3-phenyl-2-[(6-{5-phenyl-1-[4-(trifluoromethyl)benzyl]-1H-pyrrol-2-yl}-2-naphthyl)oxy]propanoate (0.200 g, 0.330 mmol), prepared in the previous step, and 1N NaOH (0.50 mL, 0.50 mmol) in 1.33:1.33:1 THF:MeOH:water (33 mL) with the exception that this reaction was not complete after 18 hours (overnight) at ambient temperature. The reaction was warmed to 30° C. for 1.5 hours, an additional portion of 1N NaOH (0.50 mL, 0.50 mmol) was added and the mixture maintained at 30° C. for an additional 1.5 hours. The isolated yellow amorphous solid was purified by reverse-phase (C18) HPLC using 20% water in acetonitrile with 0.1% formic acid as the eluent. Isolation of the product from the chromatography fractions gave 3-phenyl-2-[(6-{5-phenyl-1-[4-(trifluoromethyl)benzyl]-1H-pyrrol-2-yl}-2-naphthyl)oxy] propanoic acid as a greenish amorphous solid (0.139 g, 71%), mp 153–155° C. Elemental Analysis for $C_{37}H_{28}F_3NO_3 \cdot 0.24\ H_2O \cdot 0.10\ C_6H_{14}$ Calc'd: C, 74.70; H, 4.98; N, 2.32. Found: C, 74.67; H, 5.23; N, 2.25.

Example 9

Synthesis of 5-{[(6-{5-Phenyl-1-[4-(trifluoromethyl)benzyl]-1H-pyrrol-2-yl}-2-naphthyl)oxy]methyl}-1H-tetraazole Step 1: [(6-{5-Phenyl-1-[4-(trifluoromethyl)benzyl]-1H-pyrrol-2-yl}-2-naphthyl)oxy]acetonitrile.

In a similar manner as described in step 1 of Example 3, the title compound was prepared from 6-{5-phenyl-1-[4-(trifluoromethyl)benzyl]-1H-pyrrol-2-yl}-2-naphthol (0.250 g, 0.564 mmol), prepared in step 2 of Example 8, bromoacetonitrile (0.081 g, 0.68 mmol) and cesium carbonate (0.920 g, 2.82 mmol). Purification on a Biotage FlashElute™ system with a KP-Sil Flash 40+M column (90 g Silica Gel, 60 Å) using 50% methylene chloride in hexane as the eluent gave [(6-{5-phenyl-1-[4-(trifluoromethyl)benzyl]-1H-pyrrol-2-yl}-2-naphthyl)oxy]acetonitrile as a white solid (0.251 g, 92%), mp 154–155° C. Elemental Analysis for $C_{30}H_{21}F_3N_2O \cdot 0.10\ CH_2Cl_2$ Calc'd: C, 73.65; H, 4.35; N, 5.71. Found: C, 73.58; H, 4.46; N, 5.64.

Step 2: 5-{[(6-{5-Phenyl-1-[4-(trifluoromethyl)benzyl]-1H-pyrrol-2-yl}-2-naphthyl)oxy]methyl}-1H-tetraazole.

In a similar manner as described in step 2 of Example 3, the title compound was prepared from [(6-{5-phenyl-1-[4-(trifluoromethyl)benzyl]-1H-pyrrol-2-yl}-2-naphthyl)oxy] acetonile (0.180 g, 0.373 mmol), prepared in the previous step, ammonium chloride (0.060 g, 1.12 mmol) and sodium azide (0.073 g, 1.12 mmol) in DMF (10 mL). The reaction mixture was acidified with 1N HCl (7 mL) and partitioned against methylene chloride. The layers were separated and the aqueous layer was extracted three times with methylene chloride. The combined extracts were dried (MgSO$_4$), filtered and the solvent removed under reduced pressure to give an oil. The oil contained a large amount of DMF, so it was dissolved in EtOAc and partitioned against water. The organic layer was washed 5 times with water, dried (MgSO$_4$), filtered and the solvent removed under reduced pressure. The crude material was dissolved in methylene chloride and filtered through silica gel (95 g, 200–300 mesh). The silica gel was rinsed with one portion (500 mL) of methylene chloride and then five portions (100 mL each) of 50% methylene chloride in hexane with 1% formic acid. The filtrate portions that contained clean product were combined and the solvent was removed under reduced pressure to give 5-{[(6-{5-phenyl-1-[4-(trifluoromethyl)benzyl]-1H-pyrrol-2-yl}-2-naphthyl)oxy]methyl}-1H-tetraazole as an off-white solid (0.169 g, 86%), mp 173–175° C. Elemental Analysis for $C_{30}H_{22}F_3N_5O \cdot 0.15\ H_2O$ Calc'd: C, 68.21; H, 4.26; N, 13.26. Found: C, 68.38; H, 4.03; N, 13.22.

Example 10

Synthesis of [(6-{5-Phenyl-1-[4-(trifluoromethyl)benzyl]-1H-pyrrol-2-yl}-2-naphthyl)oxy]acetic acid Step 1: Methyl [(6-{5-phenyl-1-[4-(trifluoromethyl)benzyl]-1H-pyrrol-2-yl}-2-naphthyl)oxy]acetate.

In a similar manner as described in step 1 of Example 3, the title compound was prepared from 6-{5-phenyl-1-[4-(trifluoromethyl)benzyl]-1H-pyrrol-2-yl}-2-naphthol (0.250 g, 0.564 mmol), prepared in step 2 of Example 8, methyl bromoacetate (0.103 g, 0.676 mmol) and cesium carbonate (0.920 g, 2.82 mmol). Purification on a Biotage FlashElute™ system with a KP-Sil Flash 40+M column (90 g Silica Gel, 60 Å) using 50% methylene chloride in hexane as the eluent gave methyl [(6-{5-phenyl-1-[4-(trifluoromethyl)benzyl]-1H-pyrrol-2-yl}-2-naphthyl)oxy]acetate as an off-white solid (0.271 g, 93%), mp 90–91° C. Elemental Analysis for $C_{31}H_{24}F_3NO_3 \cdot 0.09\ C_6H_{14}$ Calc'd: C, 72.39; H, 4.87; N, 2.68. Found: C, 72.26; H, 4.68; N, 2.28.

Step 2: [(6-{5-Phenyl-1-[4-(trifluoromethyl)benzyl]-1H-pyrrol-2-yl}-2-naphthyl)oxy]acetic acid.

In a similar manner as described in step 2 of Example 6, the title compound was prepared from methyl [(6-{5-phenyl-1-[4-(trifluoromethyl)benzyl]-1H-pyrrol-2-yl}-2-naphthyl)oxy]acetate (0.20 g, 0.38 mmol), prepared in the previous step, and 1N NaOH (0.58 mL, 0.58 mmol) in 1.67:1.67:1 THF:MeOH:water (39 mL). Purification on a Biotage Horizon™ system with a KP-Sil Flash 25+M column (40 g Silica Gel, 60 Å) using 25% EtOAc in hexane with 1% formic acid as the eluent gave [(6-{5-phenyl-1-[4-(trifluoromethyl)benzyl]-1H-pyrrol-2-yl}-2-naphthyl)oxy]acetic acid as an off-white solid (0.155 g, 79%), mp 154–156° C. Elemental Analysis for $C_{30}H_{22}F_3NO_3 \cdot 0.02\ H_2O$ Calc'd: C, 71.80; H, 4.43; N, 2.79. Found: C, 71.96; H, 4.55; N, 2.61.

Example 11

Synthesis of 5-({[6-(1,5-diphenyl-1H-pyrrol-2-yl)-2-naphthyl]oxy}methyl)-1H-tetraazole Step 1: 2-(6-Methoxy-2-naphthyl)-1,5-diphenyl-1H-pyrrole.

In a similar manner as described in step 1 of Example 8, the title compound was prepared from 1-(6-methoxy-2-naphthyl)-4-phenylbutane-1,4-dione (1.50 g, 4.71 mmol), prepared in step 3 of Example 1, and aniline (3.07 g, 33.0 mmol). Purification on silica gel (500 g, 200–300 mesh) using 0% to 50% methylene chloride in hexane as the eluent gave 2-(6-methoxy-2-naphthyl)-1,5-diphenyl-1H-pyrrole as an off-white solid (1.36 g, 77%), mp 199–200° C. Elemental Analysis for $C_{27}H_{21}NO \cdot 0.11\ CH_2Cl_2$ Calc'd: C, 84.62; H, 5.56; N, 3.64. Found: C, 84.55; H, 5.67; N, 3.61.

Step 2: 6-(1,5-Diphenyl-1H-pyrrol-2-yl)-2-naphthol.

In a similar manner as described in step 5 of Example 1, the title compound was prepared from 2-(6-methoxy-2-naphthyl)-1,5-dipheny-1H-pyrrol (1.25 g, 3.33 mmol), prepared in the previous step, and pyridine hydrochloride (30 g) with the exception that this reaction required heating at 205° C. Purification on silica gel (500 g, 200–300 mesh) using methylene chloride as the eluent gave 6-(1,5-diphenyl-1H-pyrrol-2-yl)-2-naphthol as a reddish solid (1.00 g, 83%), mp 222–223° C. Elemental Analysis for $C_{26}H_{19}NO \cdot 0.11\ C_4H_8O_2$ Calc'd: C, 85.57; H, 5.40; N, 3.77. Found: C, 85.28; H, 5.53; N, 3.73.

Step 3: {[6-(1,5-Diphenyl-1H-pyrrol-2-yl)-2-naphthyl]oxy}acetonitrile.

In a similar manner as described in step 6 of Example 1, the title compound was prepared from 6-(1,5-diphenyl-1H-pyrrol-2-yl)-2-naphthol (0.200 g, 0.553 mmol), bromoacetonitrile (0.0796 g, 0.664 mmol) and cesium carbonate (0.900 g, 2.77 mmol) with the exception that the product was extracted with two portions each of methylene chloride and EtOAc. Purification on a Biotage Horizon™ system with a KP-Sil Flash 40+M column (100 g Silica Gel, 60 Å) using 55% to 95% methylene chloride in hexane as the eluent gave {[6-(1,5-diphenyl-1H-pyrrol-2-yl)-2-naphthyl]oxy}acetonitrile as a white solid (0.170 g, 77%), mp 229–230° C. Elemental Analysis for $C_{28}H_{20}N_2O$.0.05 $CH_2Cl_2$ Calc'd: C, 83.24; H, 5.01; N, 6.92. Found: C, 83.12; H, 4.77; N, 6.89.

Step 4: 5-({[6-(1,5-Diphenyl-1H-pyrrol-2-yl)-2-naphthyl]oxy}methyl)-1H-tetraazole.

In a similar manner as described in step 2 of Example 3, the title compound was prepared from {[6-(1,5-diphenyl-1H-pyrrol-2-yl)-2-naphthyl]oxy}acetonitrile (0.180 g, 0.373 mmol), prepared in the previous step, ammonium chloride (0.060 g, 1.12 mmol) and sodium azide (0.073 g, 1.12 mmol) in DMF (10 mL). The precipitated solids were isolated by vacuum filtration to give 5-({[6-(1,5-diphenyl-1H-pyrrol-2-yl)-2-naphthyl]oxy}methyl)-1H-tetraazole as an off-white solid (0.130 g, 98%), mp 269–270° C. (dec). Elemental Analysis for $C_{28}H_{21}N_5O$ Calc'd: C, 75.83; H, 4.77; N, 15.79. Found: C, 75.83; H, 4.69; N, 15.50.

Example 12

Synthesis of {[6-(1,5-diphenyl-1H-pyrrol-2-yl)-2-naphthyl]oxy}acetic acid

Step 1: Methyl {[6-(1,5-diphenyl-1H-pyrrol-2-yl)-2-naphthyl]oxy}acetate.

In a similar manner as described in step 6 of Example 1, the title compound was prepared from 6-(1,5-diphenyl-1H-pyrrol-2-yl)-2-naphthol (0.200 g, 0.553 mmol), prepared in step 2 of Example 11, methyl bromoacetate (0.102 g, 0.664 mmol) and cesium carbonate (0.900 g, 2.77 mmol) with the exception that the product was extracted with methylene chloride. Purification on a Biotage Horizon™ system with a KP-Sil Flash 40+M column (100 g Silica Gel, 60 Å) using 55% to 95% methylene chloride in hexane as the eluent gave methyl {[6-(1,5-diphenyl-1H-pyrrol-2-yl)-2-naphthyl]oxy}acetate as an off-white solid (0.22 g, 92%), mp 188–189° C. Elemental Analysis for $C_{29}H_{23}NO_3$.0.16 $CH_2Cl_2$ Calc'd: C, 78.34; H, 5.26; N, 3.13. Found: C, 77.73; H, 5.08; N, 3.07.

Step 2: {[6-(1,5-Diphenyl-1H-pyrrol-2-yl)-2-naphthyl]oxy}acetic acid.

In a similar manner as described in step 2 of Example 6, the title compound was prepared from methyl {[6-(1,5-diphenyl-1H-pyrrol-2-yl)-2-naphthyl]oxy}acetate (0.17 g, 0.39 mmol), prepar in the previous step, and 1N NaOH (0.59 mL, 0.59 mmol) in 5:5:1 THF:MeOH:water (55 mL) with the exception that this reaction required heating to 65° C. and was complete after 6 hours. The still warm reaction mixture was filtered and then allowed to cool to ambient temperature. The mixture was acidified with 1N HCl (2.5 mL) and the volatiles were removed under reduced pressure (without the addition of heat). The resulting slurry was diluted with water (25 mL) and the solids were isolated by filtration to give {[6-(1,5-diphenyl-1H-pyrrol-2-yl)-2-naphthyl]oxy}acetic acid as an off-white solid (0.148 g, 90%), mp 258–260° C. (dec). Elemental Analysis for $C_{28}H_{21}NO_3$.0.23 $H_2O$ Calc'd: C, 79.39; H, 5.11; N, 3.31. Found: C, 78.84; H 5.03; N, 3.00.

Example 13

Synthesis of 2-{[6-(1,5-diphenyl-1H-pyrrol-2-yl)-2-naphthyl]oxy}-3-phenylpropanoic acid Step 1: Methyl 2-{[6-(1,5-diphenyl-1H-pyrrol-2-yl)-2-naphthyl]oxy}-3-phenylpropanoate.

In a similar manner as described in step 1 of Example 7, the title compound was prepared from 6-(1,5-diphenyl-1H-pyrrol-2-yl)-2-naphthol (0.300 g, 0.676 mmol), prepared in step 2 of Example 11, 3-phenyl-2-trifluoromethanesulfonyloxypropionic acid methyl ester (0.317 g, 1.02 mmol) and cesium carbonate (0.441 g, 1.35 mmol) with the exception that this reaction was complete after 30 minutes at ambient temperature. Purification on a Biotage Horizon™ system with a KP-Sil Flash 25+M column (40 g Silica Gel, 60 Å) using 25% to 65% methylene chloride in hexane as the eluent gave methyl 2-{[6-(1,5-diphenyl-1H-pyrrol-2-yl)-2-naphthyl]oxy}-3-phenylpropanoate as a white solid (0.257 g, 89%), mp 178–179° C. Elemental Analysis for $C_{36}H_{29}NO_3$ Calc'd: C, 82.58; H, 5.58; N, 2.67. Found: C; 81.87; H, 5.10; N, 2.50.

Step 2: 2-{[6-(1,5-Diphenyl-1H-pyrrol-2-yl)-2-naphthyl]oxy}-3-phenylpropanoic acid.

In a similar manner as described in step 2 of Example 12, the title compound was prepared from methyl 2-{[6-(1,5-diphenyl-1H-pyrrol-2-yl)-2-naphthyl]oxy}-3-phenylpropanoate (0.186 g, 0.355 mmol), prepared in the previous step, and 1N NaOH (0.53 mL, 0.53 mmol) in 2:2:1 THF:MeOH:water (25 mL). The starting material required heating to dissolve in the THF (10 mL). After the solution was clear, MeOH (10 mL) was added followed by the water (5 mL). The reaction was complete after 2.5 hours. The solids were isolated by filtration to give 2-{[6-(1,5-diphenyl-1H-pyrrol-2-yl)-2-naphthyl]oxy}-3-phenylpropanoic acid as a beige solid (0.17 g, 94%), mp 194–196° C. (dec). Elemental Analysis for $C_{35}H_{27}NO_3$.0.23 $H_2O$ Calc'd: C, 81.83; H, 5.39; N, 2.73. Found: C, 81.07; H, 5.44; N, 2.56.

Example 14

4-{[(6-{5-phenyl-1-[4-(trifluoromethyl)benzyl]-1H-pyrrol-2-yl}-2-naphthyl)oxy]methyl}benzoic acid Step 1: methyl 4-{[(6-{5-phenyl-1-[4-(trifluoromethyl)benzyl]-1H-pyrrol-2-yl}-2-naphthyl)oxy]methyl}benzoate.

A mixture of 6-{5-phenyl-1-[4-(trifluoromethyl)benzyl]-1H-pyrrol-2-yl}-2-naphthol (250 mg, 0.564 mmol), prepared in step 2 of Example 8, methyl 4-(bromomethyl)benzoate (155 mg, 0.677 mmol) and cesium carbonate (918 mg, 2.82 mmol) in 50 mL of acetone was stirred under nitrogen at room temperature for 1.5 h. The reaction was concentrated under reduced pressure to remove the acetone. The residue was partitioned between ethyl acetate and water. The aqueous layer was separated and extracted multiple times with ethyl acetate. The combined extracts were dried ($MgSO_4$), filtered and the solvent removed under reduced pressure to give 0.36 g of a tan solid. Purification of the solid on a Biotage Horizon™ system with a KP-SIL Flash 40+M column using 50% methylene in hexane as the eluent gave methyl 4-{[(6-{5-phenyl-1-[4-(trifluoromethyl)benzyl]-1H-pyrrol-2-yl}-2-naphthyl)oxy]methyl}benzoate (260 mg, 78%) as an off-white solid, mp 154–155° C. Elemental Analysis for $C_{37}H_{28}F_3NO_3$ Calc'd: C, 75.12; H, 4.77; N, 2.37. Found: C, 75.15; H, 4.63; N, 2.30.

Step 2: 4-{[(6-{5-phenyl-1-[4-(trifluoromethyl)benzyl]-1H-pyrrol-2-yl}-2-naphthyl)oxy]methyl}benzoic acid.

A mixture of methyl 4-{[(6-{5-phenyl-1-[4-(trifluoromethyl)benzyl]-1H-pyrrol-2-yl}-2-naphthyl)oxy]methyl}benzoate (200 mg, 0.338 mmol), prepared in the previous step, and 1 N NaOH (507 μL, 0.507 mmol) in 20 mL of THF plus 20 mL of methanol plus 5 mL water was refluxed under nitrogen for 9 h. The reaction was filtered and then allowed to cool to room temperature. The reaction was acidified by the addition of 2.5 mL of 1 N HCl and then concentrated under reduced pressure to remove the THF and methanol. The residue was diluted with water. The solid formed was collected by filtration, rinsed with water and dried under reduced pressure to give the title compound (186 mg, 95%) as an off-white solid, mp 228–229° C. Elemental Analysis for $C_{36}H_{26}F_3NO_3 \cdot 0.15\ H_2O \cdot 0.04\ C_4H_8O$ Calc'd: C, 74.47; H, 4.60; N, 2.40. Found: C, 74.52; H, 4.49; N, 2.68.

Example 15

4-({[6-(1,5-diphenyl-1H-pyrrol-2-yl)-2-naphthyl]oxy}methyl)benzoic acid

Step 1: Methyl 4-({[6-(1,5-diphenyl-1H-pyrrol-2-yl)-2-naphthyl]oxy}methyl)benzoate.

A mixture of 6-(1,5-diphenyl-1H-pyrrol-2-yl)-2-naphthol (300 mg, 0.830 mmol), prepared in step 2 of Example 11, methyl 4-(bromomethyl)benzoate (228 mg, 996 mmol) and cesium carbonate (1.38 g, 4.15 mmol) in 50 mL of acetone was stirred under nitrogen at room temperature for 2.5 h. The reaction was concentrated under reduced pressure to remove the acetone. The residue was partitioned between methylene chloride and water. The aqueous layer was separated and extracted two times with methylene chloride. The combined extracts were dried ($MgSO_4$) filtered and the solvent removed under reduced pressure to give 486 mg of a tan solid. Purification of the solid on a Biotage Horizon™ system with a KP-SIL Flash 40+M column using 10% to 50% methylene chloride in hexane as the eluent gave methyl 4-({[6-(1,5-diphenyl-1H-pyrrol-2-yl)-2-naphthyl]oxy}methyl)benzoate (320 mg, 76%) as a very light red solid, mp 218–219° C. Elemental analysis for $C_{35}H_{27}NO_3$ Calc'd: C, 82.49; H, 5.34; N, 2.75. Found: C, 81.71; H, 5.23; N, 2.64.

Step 2: 4-({[6-(1,5-diphenyl-1H-pyrrol-2-yl)-2-naphthyl]oxy}methyl)benzoic acid.

A mixture of methyl 4-({[6-(1,5-diphenyl-1H-pyrrol-2-yl)-2-naphthyl]oxy}methyl)benzoate (235 mg, 0.461 mmol), prepared in the previous step, and 1 N NaOH (692 μL, 0.692 mmol) in 30 mL of THF plus 30 mL of methanol plus 5 mL of water was refluxed under nitrogen for 7 h. The reaction was filtered, cooled to room temperature, acidified by the addition of 2.5 mL of 1 N HCl and then concentrated under reduced pressure to remove the THF and methanol. The solid present was collected by filtration, rinsed with water and dried under reduced pressure to give the title compound (225 mg, 99%) as a white solid, mp 309–310° C. Elemental Analysis for $C_{34}H_{25}NO_3 \cdot 0.05\ C_4H_8O \cdot 0.19\ H_2O$ Calc'd: C, 81.73; H, 5.17; N, 2.79. Found: C, 81.94; H, 5.02; N, 2.65.

Example 16

4-{[(6-{5-phenyl-1-[4-(trifluoromethyl)benzyl]-1H-pyrrol-2-yl}-2-naphthyl)oxy]methyl}isophthalic acid Step 1: Dimethyl 4-{[(6-{5-phenyl-1-[4-(trifluoromethyl)benzyl]-1H-pyrrol-2-yl}-2-naphthyl)oxy]methyl}isophthalate.

A mixture of 6-{5-phenyl-1-[4-(trifluoromethyl)benzyl]-1H-pyrrol-2-yl}-2-naphthol (200 mg, 0.451 mmol), prepared in step 2 of Example 8, dimethyl 4-(bromomethyl)isophthalate (155 mg, 0.541 mmol) and cesium carbonate (734 mg, 2.25 mmol) in 40 mL of acetone was stirred under nitrogen at room temperature for 1.5 h. The reaction was concentrated under reduced pressure to remove the acetone. The residue was partitioned between methylene chloride and water. The aqueous layer was separated and extracted two times with methylene chloride. The combined extracts were dried ($MgSO_4$), filtered and the solvent removed under reduced pressure to give 312 mg of a yellow solid. Purification of the solid on a Biotage Horizon™ system with a KP-SIL Flash 40+M column using methylene chloride in hexane to as the eluent gave dimethyl 4-{[(6-{5-phenyl-1-[4-(trifluoromethyl)benzyl]-1H-pyrrol-2-yl}-2-naphthyl)oxy]methyl}isophthalate (200 mg, 68%) as an off-white solid, mp 172–174° C. Elemental analysis for $C_{39}H_{30}F_3NO_5$ Calc'd: C, 72.10; H, 4.65; N, 2.16. Found: C, 71.47; H, 4.22; N, 2.16.

Step 2: 4-{[(6-{5-phenyl-1-[4-(trifluoromethyl)benzyl]-1H-pyrrol-2-yl}-2-naphthyl)oxy]methyl}isophthalic acid.

A mixture of dimethyl 4-{[(6-{5-phenyl-1-[4-(trifluoromethyl)benzyl]-1H-pyrrol-2-yl}-2-naphthyl)oxy]methyl}isophthalate (165 mg, 0.254 mmol), prepared in the previous step, and 1 N NaOH (1.52 mL, 1.52 mmol) in 30 mL of THF plus 20 mL of methanol plus 5 mL of water was refluxed under nitrogen for 6 h. The reaction was filtered, cooled to room temperature, acidified by the addition of 5 mL of 1 N HCl and then concentrated under reduced pressure to remove the THF and methanol. The solid present was collected by filtration, rinsed with water and dried under reduced pressure at 60° C. to give the title compound (148 mg, 94%) as a yellow solid, mp 250–252° C. Elemental Analysis for $C_{37}H_{26}F_3NO_5 \cdot 0.18\ C_4H_8O \cdot 0.34\ H_2O$ Calc'd: C, 70.71; H, 4.42; N, 2.19. Found: C, 70.65; H, 4.34; N, 2.13.

Example 17

4-({[6-(5-phenyl-1H-pyrrol-2-yl)-2-naphthyl]oxy}methyl)isophthalic acid

Step 1: Dimethyl 4-({[6-(5-phenyl-1H-pyrrol-2-yl)-2-naphthyl]oxy}methyl)isophthalate.

A mixture of 6-(5-phenyl-1H-pyrrol-2-yl)-2-naphthol (200 mg, 0.701 mmol), prepared in step 5 of Example 1, dimethyl 4-(bromomethyl)isophthalate (241 mg, 0.841 mmol) and cesium carbonate (1.14 g, 3.50 mmol) in 50 mL of acetone was stirred at room temperature for 1.5 h. The reaction was concentrated under reduced pressure to remove the acetone. The residue was partitioned between methylene chloride and water. The aqueous layer was separated and extracted two times with methylene chloride. The combined extracts were dried ($MgSO_4$), filtered and the solvent removed under reduced pressure to give a yellow solid. Purification of the solid on a Biotage Horizon™ system with a KP-SIL Flash 40+M column using a gradient of 85% methylene chloride in hexane to 100% methylene chloride as the eluent gave dimethyl 4-({[6-(5-phenyl-1H-pyrrol-2-yl)-2-naphthyl]oxy}methyl)isophthalate (280 mg, 81%) as a yellow solid, mp 203–205° C. Elemental Analysis for $C_{31}H_{25}NO_5 \cdot 0.10$ $CH_2Cl_2$ Calc'd: C, 74.70; H, 5.08; N, 2.80. Found: C, 74.24; H, 4.80; N, 2.76.

Step 2: 4-({[6-(5-phenyl-1H-pyrrol-2-yl)-2-naphthyl]oxy}methyl)isophthalic acid:

A mixture of dimethyl 4-({[6-(5-phenyl-1H-pyrrol-2-yl)-2-naphthyl]oxy}methyl)isophthalate (230 mg, 0.468 mmol), prepared in the previous step, and 1 N NaOH (2.81 mL, 2.81 mmol) in 30 mL of THF plus 20 mL of methanol plus 5 mL of water was refluxed under nitrogen for 7 h. The reaction was filtered, cooled to room temperature, acidified by the addition of 5 mL of 1 N HCl and then concentrated under reduced pressure to remove the THF and methanol. The solid present was collected by filtration, rinsed with water and dried under reduced pressure at 60° C. to give the title compound (204 mg, 94%) as a yellow solid, mp 289–291° C. Elemental Analysis for $C_{29}H_{21}NO_5 \cdot 0.40$ $C_4H_8O \cdot 0.22$ $H_2O$ Calc'd: C, 74.06; H, 5.00; N, 2.82. Found: C, 73.83; H, 5.19; N, 2.70.

Example 18

Primary Screen for the PAI-1 Inhibition

Test compounds are dissolved in DMSO at a final concentration of 10 mM, then diluted 100× in physiologic buffer. The inhibitory assay is initiated by the addition of the test compound (1–100 µM final concentration, maximun DMSO concentration of 0.2%) in a pH 6.6 buffer containing 140 nM recombinant human plasminogen activator inhibitor-1 (PAI-1; Molecular Innovations, Royal Oak, Mich.). Following a 1 hour incubation at room temperature, 70 nM of recombinant human tissue plasminogen activator (tPA) is added, and the combination of the test compound, PAI-1 and tPA is incubated for an additional 30 minutes. Following the second incubation, Spectrozyme-tPA (*American Diagnostica*, Greenwich, Conn.), a chromogenic substrate for tPA, is added and absorbance read at 405 nm at 0 and 60 minutes. Relative PAI-1 inhibition is equal to the residual tPA activity in the presence of the test compound and PAI-1. Control treatments include the complete inhibition of tPA by PAI-1 at the molar ratio employed (2:1), and the absence of any effect of the test compound on tPA alone.

Example 19

Assay for Determining $IC_{50}$ of Inhibition of PAI-1

This assay is based upon the non-SDS dissociable interaction between tPA and active PAI-1. Assay plates are initially coated with human tPA (10 µg/ml). Test compounds of the present invention are dissolved in DMSO at 10 mM, then diluted with physiologic buffer (pH 7.5) to a final concentration of 1–50 µM. Test compounds are incubated with human PAI-1 (50 ng/ml) for 15 minutes at room temperature. The tPA-coated plate is washed with a solution of 0.05% Tween 20 and 0.1% BSA, then the plate is blocked with a solution of 3% BSA. An aliquot of the pyrrolonaphthyl/PAI-1 solution is then added to the tPA-coated plate, incubated at room temperature for 1 hour, and washed. Active PAI-1 bound to the plate is assessed by adding an aliquot of a 1:1000 dilution of the 33B8 monoclonal antibody against human PAI-1, and incubating the plate at room temperature for 1 hour (Molecular Innovations, Royal Oak, Mich.). The plate is again washed, and a solution of goat anti-mouse IgG-alkaline phosphatase conjugate is added at a 1:50,000 dilution in goat serum. The plate is incubated 30 minutes at room temperature, washed, and a solution of alkaline phosphatase substrate is added. The plate is incubated 45 minutes at room temperature, and color development is determined at $OD_{405\ nm}$. The quantitation of active PAI-1 bound to tPA at varying concentrations of the test compound is used to determine the $IC_{50}$. Results are analyzed using a logarithmic best-fit equation. The assay sensitivity is 5 ng/ml of human PAI-1 as determined from a standard curve ranging from 0–100 ng/ml.

The compounds of the present invention inhibited Plasminogen Activator Inhibitor-1 as summarized in Table 1.

TABLE I

| Example | $IC_{50}$ (Antibody)[a] µM | % Inhibition 25 µM | % Inhibition 10 µM |
|---|---|---|---|
| 1 | 44.4 | 78 | 12 |
| 2 | 16.1 | 66 | 37 |
| 3 | 33.02 | 52 | 15 |
| 4 | | 67 | 11 |
| 5 | | 32 | 15 |
| 6 | | 74 | 14 |
| 7 | | 95 | 30 |
| 8 | | 62 | 43 |
| 9 | | 49 | 31 |
| 10 | | 55 | 29 |
| 11 | | 68 | 30 |
| 12 | | 58 | 48 |
| 13 | | 60 | 33 |
| 14 | | 31 | 23 |
| 15 | | 68 | 30 |
| 16 | | 63 | 40 |
| 17 | | 44 | 18 |

[a]The $IC_{50}$ was determined by the Antibody Assay as described above.

Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

All publications and patent documents cited above are hereby incorporated by reference in their entirety for all purposes to the same extent as if each were so individually denoted.

What is claimed:

1. A compound of Formula 4:

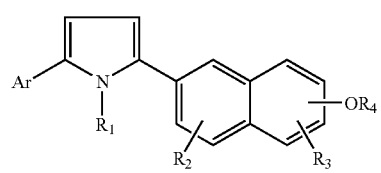

Formula 4 or a solvate, hydrate or pharmaceutically acceptable salt or ester form thereof; wherein:

Ar is aryl;

$R_1$ is hydrogen, $C_1$–$C_{12}$ alkyl, $C_{6-14}$ aryl, $C_{6-14}$ar($C_{1-6}$) alkyl, —($CH_2$)$_p$-heteroaryl, —($CH_2$)$_p$—CO-aryl, —(CH$_2$)$_p$—CO-heteroaryl, —(CH$_2$)$_p$—CO—(C$_1$–C$_6$) alkyl, C$_2$–C$_7$ alkenyl, C$_2$–C$_7$ alkynyl, or C$_3$–C$_8$ cycloalkyl, R$_2$ and R$_3$ are independently hydrogen, C$_1$–C$_{12}$ alkyl, C$_{6-14}$ aryl, C$_{6-14}$ar(C$_{1-6}$)alkyl, —(CH$_2$)$_p$-heteroaryl, halogen, C$_1$–C$_6$ alkoxy, aralkyl, alkoxyaryl, nitro, carboxy(C$_1$–C$_6$ alkyl), carbamide, carbamate, or C$_3$–C$_8$ cycloalkyl;

R$_4$ is —CH(R$_6$)(CH$_2$)$_n$R$_5$, —C(CH$_3$)$_2$R$_6$, —CH(R$_5$)(CH$_2$)$_n$R$_6$, —CH(R$_5$)C$_6$H$_4$R$_6$, —CH(R$_5$)C$_6$H$_3$(CO$_2$H)$_2$, or CH(R$_5$)C$_6$H$_2$(CO$_2$H)$_3$;

R$_5$ is hydrogen, C$_1$–C$_6$ alkyl, C$_6$–C$_{12}$ aryl, aralkyl, C$_3$–C$_8$ cycloalkyl, or —(CH$_2$)$_n$(R$_7$);

R$_6$ is CO$_2$H or tetrazole;

R$_7$ is

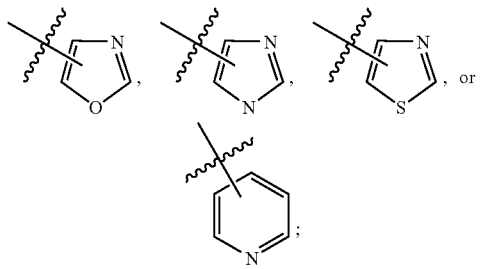

n is from 0 to 6; and
p is from 0 to 3.

2. The compound of claim 1 wherein C$_{1-12}$ alkyl is unsubstituted C$_{1-12}$ alkyl or C$_{1-3}$ perfluoroalkyl; C$_{1-6}$ alkoxy is unsubstituted C$_{1-6}$ alkoxy or C$_{1-3}$ perfluoroalkoxy; and said aralkyl group is unsubstituted benzyl or benzyl substituted with from 1 to 3 groups selected from the group consisting of C$_1$–C$_6$ alkyl, C$_1$–C$_6$ alkoxy, hydroxy, C$_3$–C$_6$ cycloalkyl, —(CH$_2$)$_p$–C$_3$–C$_6$ cycloalkyl, halogen, C$_1$–C$_3$ perfluoroalkyl, C$_1$–C$_3$ perfluoroalkoxy, —(CH$_2$)$_p$-phenyl, and —O(CH$_2$)$_p$-phenyl.

3. The compound of claim 1 having Formula 5:

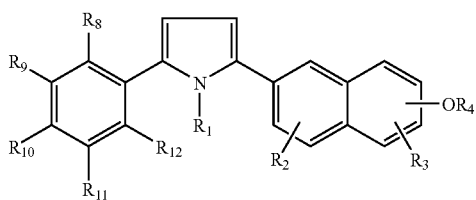

Formula 5 or a solvate, hydrate or pharmaceutically acceptable salt or ester form thereof wherein R$_8$, R$_9$, R$_{10}$, R$_{11}$ and R$_{12}$ are independently hydrogen, C$_1$–C$_6$ alkyl, C$_1$–C$_6$ alkoxy, hydroxy, C$_{6-14}$ar(C$_{1-6}$)alkyl, C$_3$–C$_6$ cycloalkyl, —(CH$_2$)$_p$—C$_3$–C$_6$ cycloalkyl, halogen, —(CH$_2$)$_p$-phenyl, or —O(CH$_2$)$_p$-phenyl.

4. The compound of claim 3 wherein C$_{1-6}$ alkyl is unsubstituted C$_{1-6}$ alkyl or C$_{1-3}$ perfluoroalkyl and C$_{1-6}$ alkoxy is unsubstituted C$_{1-6}$ alkoxy or C$_{1-3}$ perfluoroalkoxy.

5. The compound of claim 1, wherein:

Ar aryl;
R$_1$ is hydrogen, C$_1$–C$_6$ alkyl or —(CH$_2$)$_p$-phenyl;

R$_2$ and R$_3$ are independently hydrogen, unsubstituted C$_1$–C$_6$ alkyl, phenyl-(CH$_2$)$_p$-, halogen or C$_1$–C$_1$ perfluoroalkyl;

R$_4$ is —CHR$_5$CO$_2$H, —CHR$_5$C$_6$H$_4$CO$_2$H, —CHR$_5$C$_6$H$_3$(CO$_2$H)$_2$, or —CH$_2$-tetrazole;

R$_5$ is hydrogen, phenyl, or benzyl, and p is from 0 to 3.

6. The compound of claim 1 wherein Ar is phenyl, naphthyl, or fluorenyl.

7. The compound of claim 1 wherein R$_4$ is —CHR$_5$CO$_2$H.

8. The compound of claim 1 wherein R$_4$ is —(C$_2$)-tetrazole.

9. The compound of claim 1 wherein R$_4$ is —CH(R$_5$)C$_6$H$_4$CO$_2$H.

10. The compound of claim 1 that is 3-phenyl-2-{[6-(5-phenyl-1H-pyrrol-2-yl)-2-naphthyl]oxy}propanoic acid or a pharmaceutically acceptable salt or ester form thereof;

2-{[6-(1-benzyl-5-phenyl-1H-pyrrol-2-yl)-2-naphthyl]oxy}-3-phenylpropanoic acid or a pharmaceutically acceptable salt or ester form thereof; {[6-(1-benzyl-5-phenyl-1H-pyrrol-2-yl)-2-naphthyl]oxy}acetic acid or a pharmaceutically acceptable salt or ester form thereof;

2-{[6(1-methyl-5-phenyl-1H-pyrrol-2-yl)-2-naphthyl]oxy}-3-phenylpropanoic acid or a pharmaceutically acceptable salt or ester form thereof or 3-phenyl-2-[(6-{5-phenyl-1-[4-(trifluoromethyl)benzyl]-1H-pyrrol-2-yl}-2-naphthyl)oxy]proppanoic acid or
a pharmaceutically acceptable salt or ester form thereof.

11. The compound of claim 1 that is

[(6-{5-phenyl-1-[4-(trifluoromethyl)benzyl]-1H-pyrrol-2-yl}-2naphthyl)oxy]acetic acid or or a pharmaceutically acceptable salt or ester form thereof;

{[6-(1,5-diphenyl-1H-pyrrol-2yl )-2-naphthyl]oxy}acetic acid or a pharmaceutically acceptable salt or ester form thereof;

2-{[6-(1,5-diphenyl-1H-pyrrol-2-yl)-2-naphthyl]oxy}-3-phenylpropanoic acid or a pharmaceutically acceptable salt or ester form thereof;

5-({[6-(5-phenyl-1H-pyrrol-2-yl)-2-napthyl]oxy}methyl)-1H-tetraazole or a pharmaceutically acceptable salt or ester form thereof or 5-({[6-(1-benzyl-5-phenyl-1H-pyrrol-2-yl)-2-naphthyl]oxy}methyl)-1H-tetraazole or a pharmaceutically acceptable salt or ester form thereof.

12. The compound of claim 1 that is 5-({[6-(1-methyl-5-phenyl-1H-pyrrol-2-yl)-2-naphthyl]oxy}methyl)-1H-tetraazole or a pharmaceutically acceptable salt or ester form thereof;

5-{[(6-{5-phenyl-1-[4-(trifluoromethyl)benzyl]-1H-pyrrol-2-yl}-2-naphthyl)oxy]methyl}-1H-tetraazole or a pharmaceutically acceptable salt or ester form thereof;

5-({[6-(1,5-diphenyl-1H-pyrrol-2-yl)-2-naphthyl]oxy}methyl)-1H-tetraazole or a pharmaceutically acceptable salt or ester form thereof;

4-{[(6-{5-phenyl-1-[4-(trifluoromethyl)benzyl]-1H-pyrrol-2-yl}-2-naphthyl)oxy]methyl}benzoic acid or a pharmaceutically acceptable salt or ester form thereof or 4-({[6-(1,5-diphenyl-1H-pyrrol-2-yl)-2-naphthyl]oxy}methyl)benzoic acid or a pharmaceutically acceptable salt or ester form thereof.

13. The compound of claim 1 that is
4-{[(6-{5-phenyl-1-[4-(trifluoromethyl)benzyl]-1H-pyrrol-2-yl}-2-naphthyl)oxy]methyl}isophthalic acid or a pharmaceutically acceptable salt or ester form thereof or
4-({[6-(5-phenyl-1H-pyrrol-2-yl)-2-naphthyl]oxy}methyl)isophthalic acid or a pharmaceutically acceptable salt or ester form thereof.

14. A method for treating thrombosis, atrial fibrillation, pulmonary fibrosis, myocardial isehemia, strokes, thromboembolic complication of surgery, or renal fibrosis, comprising administering to a subject in need thereof a therapeutically effective amount of the compound of claim 1.

15. The method of claim 14 wherein the therapeutically effective amount is from about 25 mg/kg/day to about 200 mg/kg/day.

16. The method of claim 14 wherein the thrombosis is selected from the group consisting of venous thrombosis, arterial thrombosis, cerebral thrombosis, and deep vein thrombosis.

17. A pharmaceutical composition comprising a compound of claim 1, or a pharmaceutically acceptable salt or ester form thereof, and a pharmaceutically acceptable excipient or carrier.

18. The method of claim 14 wherein the method is for treating thrombosis.

19. The method of claim 14 wherein the method is for treating atrial fibrillation.

20. The method of claim 14 wherein the method is for treating pulmonary fibrosis.

21. The method of claim 14 wherein the method is for treating myocardial ischemia.

22. The method of claim 14 wherein the method is for treating stroke.

23. The method of claim 14 wherein the meted is for treating thromboembolic complication of surgery.

24. The method of claim 14 wherein the method is for treating renal fibrosis.

* * * * *